US012559864B2

(12) United States Patent
He et al.

(10) Patent No.: US 12,559,864 B2
(45) Date of Patent: Feb. 24, 2026

(54) PLATFORM FOR DISCOVERY AND ANALYSIS OF THERAPEUTIC AGENTS

(71) Applicant: Illumina, Inc., San Diego, CA (US)

(72) Inventors: Molly He, San Diego, CA (US); Michael Previte, San Diego, CA (US); Misha Golynskiy, San Diego, CA (US); Matthew William Kellinger, San Diego, CA (US); Sergio Peisajovich, San Diego, CA (US); Jonathan Mark Boutell, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 19/028,468

(22) Filed: Jan. 17, 2025

(65) Prior Publication Data

US 2025/0171929 A1 May 29, 2025

Related U.S. Application Data

(63) Continuation of application No. 18/368,496, filed on Sep. 14, 2023, which is a continuation of application (Continued)

(51) Int. Cl.
*C40B 50/16* (2006.01)
*B01J 19/00* (2006.01)
(Continued)

(52) U.S. Cl.
CPC ........... *C40B 50/16* (2013.01); *B01J 19/0046* (2013.01); *B01L 3/5085* (2013.01); *B01L 3/54* (2013.01);
(Continued)

(58) Field of Classification Search
CPC .......... B01J 19/0046; B01J 2219/00317; B01J 2219/00459; B01J 2219/005;
(Continued)

(56) References Cited

U.S. PATENT DOCUMENTS 6,936,469 B2   8/2005   deJong et al.
7,947,447 B2   5/2011   Zichi et al.
(Continued)

FOREIGN PATENT DOCUMENTS

EP   2805769 A1   11/2014
JP   2011516072 A   5/2011
(Continued)

OTHER PUBLICATIONS

Kazane et al. (Proc. Natl. Acad. Sci., 2012, 10:3731-3736) (Year: 2012).*

(Continued)

*Primary Examiner* — Jeremy C Flinders
(74) *Attorney, Agent, or Firm* — Gavrilovich, Dodd & Lindsey LLP

(57) ABSTRACT

A method of characterizing candidate agents including steps of (a) providing a library of candidate agents attached to nucleic acid tags; (b) contacting the library with a solid support to attach the candidate agents to the solid support, whereby an array of candidate agents is formed; (c) contacting the array with a screening agent, wherein one or more candidate agents in the array react with the screening agent; (d) detecting the array to determine that at least one candidate agent in the array reacts with the screening agent; (e) sequencing the nucleic acid tag to determine the tag sequences attached to candidate agents in the array; and (f) identifying the at least one candidate agent in the array that reacts with the screening agent based on the tag sequence that is attached to the at least one candidate agent.

24 Claims, 14 Drawing Sheets

Related U.S. Application Data

No. 16/158,120, filed on Oct. 11, 2018, now Pat. No. 11,795,581, which is a continuation of application No. 15/572,718, filed as application No. PCT/US2016/031524 on May 9, 2016, now abandoned.

(60) Provisional application No. 62/159,710, filed on May 11, 2015.

(51) Int. Cl.

| | |
|---|---|
| *B01L 3/00* | (2006.01) |
| *C12N 15/10* | (2006.01) |
| *C40B 20/04* | (2006.01) |

(52) U.S. Cl.
CPC ..... *C12N 15/1062* (2013.01); *C12N 15/1065* (2013.01); *C12N 15/1068* (2013.01); *C12N 15/1075* (2013.01); *C40B 20/04* (2013.01); *B01J 2219/00317* (2013.01); *B01J 2219/00459* (2013.01); *B01J 2219/005* (2013.01); *B01J 2219/00527* (2013.01); *B01J 2219/00547* (2013.01); *B01J 2219/00572* (2013.01); *B01J 2219/00626* (2013.01); *B01J 2219/00743* (2013.01); *B01L 2300/021* (2013.01)

(58) Field of Classification Search
CPC .... B01J 2219/00527; B01J 2219/00547; B01J 2219/00572; B01J 2219/00626; B01J 2219/00743; B01L 3/5085; B01L 3/54; C12N 15/10; C12N 15/1062; C12N 15/1065; C12N 15/1068; C12N 15/1075; C12Q 1/68; C12Q 1/6869; C12Q 2563/131; C12Q 2563/179; C12Q 2565/514; C12Q 2565/515; C40B 20/04; C40B 50/16; G01N 33/53; G01N 33/58; G01N 33/68
See application file for complete search history.

(56) References Cited

U.S. PATENT DOCUMENTS

| | | | |
|---|---|---|---|
| 8,460,864 | B2 | 6/2013 | Chee et al. |
| 8,460,865 | B2 | 6/2013 | Chee et al. |
| 8,481,903 | B2 | 7/2013 | Triener et al. |
| 11,479,808 | B2 | 10/2022 | Rawlings et al. |
| 2004/0018491 | A1 | 1/2004 | Gunderson et al. |
| 2011/0136099 | A1 | 6/2011 | Schneider et al. |
| 2013/0310280 | A1 | 11/2013 | Chee et al. |
| 2014/0228223 | A1 | 8/2014 | Gnirke et al. |
| 2015/0057162 | A1 | 2/2015 | Ullman et al. |
| 2017/0107566 | A1 | 4/2017 | Church et al. |

FOREIGN PATENT DOCUMENTS

| | | | |
|---|---|---|---|
| WO | 9955886 | A1 | 11/1999 |
| WO | 2009023107 | A1 | 2/2009 |
| WO | 2011071943 | A1 | 6/2011 |
| WO | 2012139110 | A2 | 10/2012 |
| WO | 2013096777 | A1 | 6/2013 |
| WO | 2013096777 | A2 | 6/2013 |
| WO | 2013136095 | A1 | 9/2013 |
| WO | 2014059370 | A1 | 4/2014 |
| WO | 2014083205 | A1 | 6/2014 |
| WO | 2014144822 | A2 | 9/2014 |
| WO | 2014189768 | A1 | 11/2014 |
| WO | 2015031691 | A1 | 3/2015 |
| WO | 2015066635 | A1 | 5/2015 |
| WO | 2016007063 | A1 | 1/2016 |

OTHER PUBLICATIONS

Gustafson et al. (Electrophoresis, 2022, 43:1784-1798) (Year: 2022).*
Sarkar et al. (Trends in Biotechnology, 2017, 35(3):186-189) (Year: 2017).*
Weber et al. (Biomacromolecules, 2014, 15:4621-4626) (Year: 2014).*
Lovatt et al. (Nature Methods, 2014, 11(2): 190-199) (Year: 2014).*
Lee et al. (Nature Protocols, 2015, 10(3):442-458) (Year: 2015).*
Ashili et al., "Automated platform for multiparameter stimulus response studies of metabolic activity at the single-cell level," Proc. SPIE 7929, Microfluidics, BioMEMS, and Medical Microsystems IX, 79290S (Feb. 14, 2011).
Chen et al., "Toward a solid-phase nucleic acid hybridization assay within microfluidic channels using immobilized quantum dots as donors in fluorescence resonance energy transfer," Anal Bioanal Chem, Jan. 2011, 399(1):133-41.
Lachance, Pascal, Office Action, Canadian Intellectual Property Office, Application No. 3, 160, 383, May 25, 2023.
Alberti et al., "Biomolecular self-assembly of micrometer sized silica beadson patterned glass substrates", Applied Surface Science, vol. 255, No. 17, pp. 7759-7765, Jun. 15, 2009.
Aslund, Fredrick, Extended European Patent Application, European Patent Office, Application No. 20191289.6, Oct. 5, 2020.
Aslund, Fredrick, Extended European Patent Application, European Patent Office, Application No. 20216661.7, Mar. 10, 2021.
Bose, Sayantan et al., "Scalable microfluidics for single-cell RNA printing and sequencing", Genome Biology, vol. 16, No. 120, Jan. 1, 2015, pp. 1-16.
Bowman et al., "Multiplexed Illumina sequencing libraries from picogram quantities of DNA", Bio Med Central Genomics, vol. 14, Article 466, pp. 1-7, Jul. 9, 2013.
Gu et al., "Multiplex single-molecule interaction profiling of DNA-barcoded proteins", Nature, vol. 515, pp. 554-557, Nov. 27, 2014.
Hasegawa, T., Office Action, Japan Patent Office, Application No. 2022-014932, Apr. 4, 2023.
Kim et al., Authorized Officer, Korean Intellectual Property Office, International Search Report and Written Opinion, Aug. 9, 2016, 18 pages.
Licciulli, Silvia et al., "WT1: a weak spot in KRAS-induced transformation", The Journal of Clinical Investigation, vol. 120, No. 11, Nov. 1, 2010, pp. 3804-3807.
Needels et al., "Generation and Screening of an Oligonucleotide-Encoded Synthetic Peptide Library", PNAS, vol. 90 No. 22, pp. 10700-10704, Nov. 15, 1993.
Orenshtein, Liya, Office Action, Application No. 290908, Israel Patent Office, Sep. 14, 2022.
Schwarzmuller, Tobias et al., "Systematic Phenotyping of a Large-Scale Candida glabrata Deletion Collection Reveals Novel Antifungal Tolerance Genes", PLOS Pathogens, vol. 10, No. 6, Jun. 1, 2014, p. e1004211.
Seelig et al., "Selection and evolution of enzymes from a partially randomized non-catalytic scaffold", Nature, 448, 828-833, Aug. 16, 2007.
Valencia et al., "In vitro selection of proteins with desired charac-teristics using mRNA-display", Methods, vol. 60, No. 1, pp. 55-69, Mar. 15, 2013.
Weng et al., "Generating addressable protein microarrays with PROfusion™ covalent mRNA-protein fusion technology", Proteomics, vol. 2, No. 1, pp. 48-57, Jan. 10, 2002.
Zhu et al., "Enzymatic Profiling System in a Small-Molecule Microarray", Organic Letters, vol. 5, No. 8, pp. 1257-1260 Apr. 17, 2003.

* cited by examiner

Step 1: Synthesize 500,000 29-mer oligos + attachment group (-SH, amine; NHS).
1.    Synthesizer = 50,000 oligos/day   500,000 oligos in 10 days
2.    Bar-code = 19-mer; "Primer" = 10-mer Step 2: Ligate overhang primer with monotemplate sequence in individual wells Step 3: Robotically add compounds with reactive group (RG) to individual wells with functionalized codes.

Step 4: Immobilize compounds via hybridization or surface functional group to Single Molecule surface (or Pazam flow cell surface).

Step 5: Flow in target molecules and record real-time images of binding kinetics to compounds.

Multi-labeled Target

Step 6: Sequence encoded molecules to identify "leads" or "hits".

P5     cDNA library     P7

⌐➤ = transcription/translation
      initiation sites

1. Make library (eg.fragmented cDNA) -
adaptor sequence includes
transcription initiation site and start
codon 2. Make clusters ribosome protein 5. Sequence clusters ←——— 4. Assay for protein ←——— 
to identify positives          activity of interest
from step 4

RNA
pol

RNA
pol

3. Transcribe and translate

1. Create bacterial library with mRNA transcripts + index (index: 10bp = $10^6$ codes; 20 bp = $10^{12}$ codes)

2. Lyse Bacteria - collect mRNA transcripts 3. 1/2 sample → Sequencing determine indices for mutations.

$$\text{Mutation } Y_1 = \text{Code } X_1$$
$$\text{Mutation } Y_2 = \text{Code } X_2$$
$$\text{Mutation } Y_N = \text{Code } X_N$$

4. 1/2 sample → on flow cell translation/assay

Load single cells
into each well

Add individual
barcode to each well

PLATFORM FOR DISCOVERY AND ANALYSIS OF THERAPEUTIC AGENTS

CROSS REFERENCE TO RELATED APPLICATIONS

This application is a continuation application of U.S. patent application Ser. No. 18/368,496, filed on Sep. 14, 2023, which is a continuation application of U.S. patent application Ser. No. 16/158,120, filed on Oct. 11, 2018, now U.S. Pat. No. 11,795,581, which is a continuation application of U.S. application Ser. No. 15/572,718, filed on Nov. 8, 2017, which is a 35 U.S.C. § 371 National Stage application of International Patent Application No. PCT/US2016/031524, filed on May 9, 2016, which further claims the benefit of priority to U.S. Provisional Patent Application No. 62/159,710, filed May 11, 2015, each of which is hereby incorporated by reference in its entirety.

BACKGROUND

This disclosure relates generally to discovery of agents (e.g. small molecules, proteins or cells) having medical, agricultural, and industrial uses, and more specifically to platforms for screening candidate agents for such uses.

Currently, high throughput screening drug discovery utilizes multiple steps and platforms to screen large libraries of small molecules for "leads" or "hits" that show efficacy and potency against a particular target, as well as a favorable toxicity profile against a panel of molecular targets.

In the first step in the process, a small molecule library is screened in a high throughput fashion against a pre-determined target. These libraries are typically on the order of hundreds of thousands of compounds. Current high throughput methodologies can be automated. As a result, of the evolution of robotics and automation, high cost instrumentation can screen 100,000 molecules/day using volumes of input reagent in the low microliter range. The assays can be either homogeneous or heterogeneous, the former being relatively simple and affordable and the latter being more sensitive albeit more complex, time consuming and expensive.

While the initial small molecule screening assays are effective in identifying "hits" or "leads", these assays are typically only a first step. These leads or hits are typically screened further with respect to genotoxicity, pharmacological toxicity, cellular toxicity, and organism cytotoxicity using profiling assays against well-defined targets to eliminate candidates that may have adverse clinical effects. Each of these assays is independently performed using a variety of platforms and kitted assays that employ independent workflows that are curated and data mined to generate a consensus on the utility of the hit or lead.

Protein evolution methods constitute another type of screen t. These methodologies have covered a vast array of permutations. While the throughput, speed and low cost of these methodologies have tended to make them a leading choice for rapid protein evolution, the methods are often complex and wrought with challenges. For example, emulsion based screens raise difficulties with merging/mixing droplets (for multiplexed screening), difficulties with breaking emulsions (recovering components of interest), complications arising from concentration variation due to varying droplet sizes, and cross-contamination of droplets.

Cell-based therapies have therapeutic capabilities that are potentially advantageous compared to small molecule-based or protein-based therapies. Among the key advantages: cells can sense external signals, move to specific sites within the body, and integrate multiple stimuli and respond with complex behaviors (such as the release of specific effector molecules). Fully achieving the potential of cell-based therapeutics will benefit from precisely engineering therapeutic cells so that their "behaviors" can be controlled both in space and time.

Current workflows in cellular engineering typically include the following steps: (i) design of intracellular signaling circuits responsible for sensing, integrating and responding to stimuli; (ii) complex genetic engineering to incorporate the genes responsible for mediating those functions in the cell; and (iii) screening methods to identify among all cells in the library, those carrying the gene complement that better performs the desired function. Because of the complexity of the desired cellular behaviors, current screening methods are not ideal. For example: fluorescence activated cell sorting (FACS)-based methods are high-throughput but only look at snapshots of cellular behavior. Fluorescence microscopy on the other hand, can follow the dynamics of cellular behaviors in detail, but are low throughput.

Thus, there exists a need for platforms and methods to screen small molecules, proteins, cells and other agents for beneficial properties. The present disclosure addresses this need and provides other advantages as well.

BRIEF SUMMARY

The present disclosure provides a method of characterizing candidate agents. The method can include the steps of (a) providing a library of candidate agents, wherein each candidate agent is attached to a nucleic acid tag having a tag sequence; (b) contacting the library of candidate agents with a solid support to attach the candidate agents to the solid support, whereby an array of candidate agents is formed including individual features on the solid support that each attach to an individual candidate agent from the library; (c) contacting the array of candidate agents with a screening agent, wherein one or more candidate agents in the array react with the screening agent; (d) detecting the array during or after the contacting of the array with the screening agent, thereby determining that at least one candidate agent in the array reacts with the screening agent; (e) sequencing the nucleic acid tags on the array to determine the tag sequence that is attached to each of the candidate agents; and (f) identifying the at least one candidate agent in the array that reacts with the screening agent based on the tag sequence that is attached to the at least one candidate agent.

This disclosure further provides a method for producing an array of proteins. The method can include steps of (a) providing a library of cDNA molecules that are attached to a solid support; (b) amplifying the cDNA molecules on the solid support to form clusters, wherein each cluster includes multiple copies of a particular cDNA molecule from the library; (c) transcribing the multiple copies at the clusters to produce multiple mRNA molecules attached to each of the clusters; and (d) translating the mRNA molecules at the clusters to produce multiple proteins attached to each of the clusters.

This disclosure also provides a method for producing an array of proteins that includes steps of (a) providing a library of mRNA molecules, wherein individual mRNA molecules in the library include a target sequence and a tag sequence, (b) deriving a first sub-library from the library, the first sub-library including nucleic acids having the tag sequences or complements thereof, wherein the nucleic acids are attached to individual features on a solid support, (c) deriving a second sub-library from the library, the second sub-library including nucleic acids having the target sequences and the tag sequences or complements thereof; (d) contacting the second sub-library with the first sub-library, thereby attaching nucleic acids of the second sub-library to the solid support via hybridization of the tag sequences and the complements thereof; and (e) translating the target sequences on the solid support to produce an array of proteins attached to the individual features.

Also provided by this disclosure is a method of screening cells. The method can include the steps of (a) providing a plurality of different cells, wherein each of the different cells includes a nucleic acid tag having a tag sequence; (b) contacting a mixture of the different cells with a solid support to form an array of cells attached to the solid support; (c) screening the array of cells on the solid support for at least one optical characteristic, wherein the screening reaction includes detecting the individual cells that are attached to the solid support; (d) sequencing the tag sequences of nucleic acid tags that are attached to the solid support; and (e) identifying at least one cell in the array as a candidate cell based on the optical characteristic and the tag sequence of the candidate cell.

This disclosure provides an array that includes (a) a solid support; (b) a library of different cDNA molecules attached to the solid support, wherein each different cDNA molecule is attached to an individual feature on the solid support, and wherein each feature includes multiple copies of a particular cDNA molecule (c) mRNA molecules attached to the cDNA molecules, wherein each of the cDNA molecules is complementary to the respective attached mRNA molecule; and (d) protein molecules attached to the mRNA molecules, wherein each of the protein molecules is encoded by the respective attached mRNA molecule.

This disclosure further provides an array that includes (a) a library of mRNA molecules, wherein individual mRNA molecules in the library comprise a target sequence and a tag sequence, (b) a solid support comprising nucleic acids having complements of the tag sequences, wherein the nucleic acids are attached to individual features on a solid support, wherein the tag sequences of the individual mRNA molecules are hybridized to respective complementary tag sequences at the individual features on the solid support, and wherein proteins derived by translation of the mRNA molecules are attached to respective mRNA molecules.

4

Figure 9:
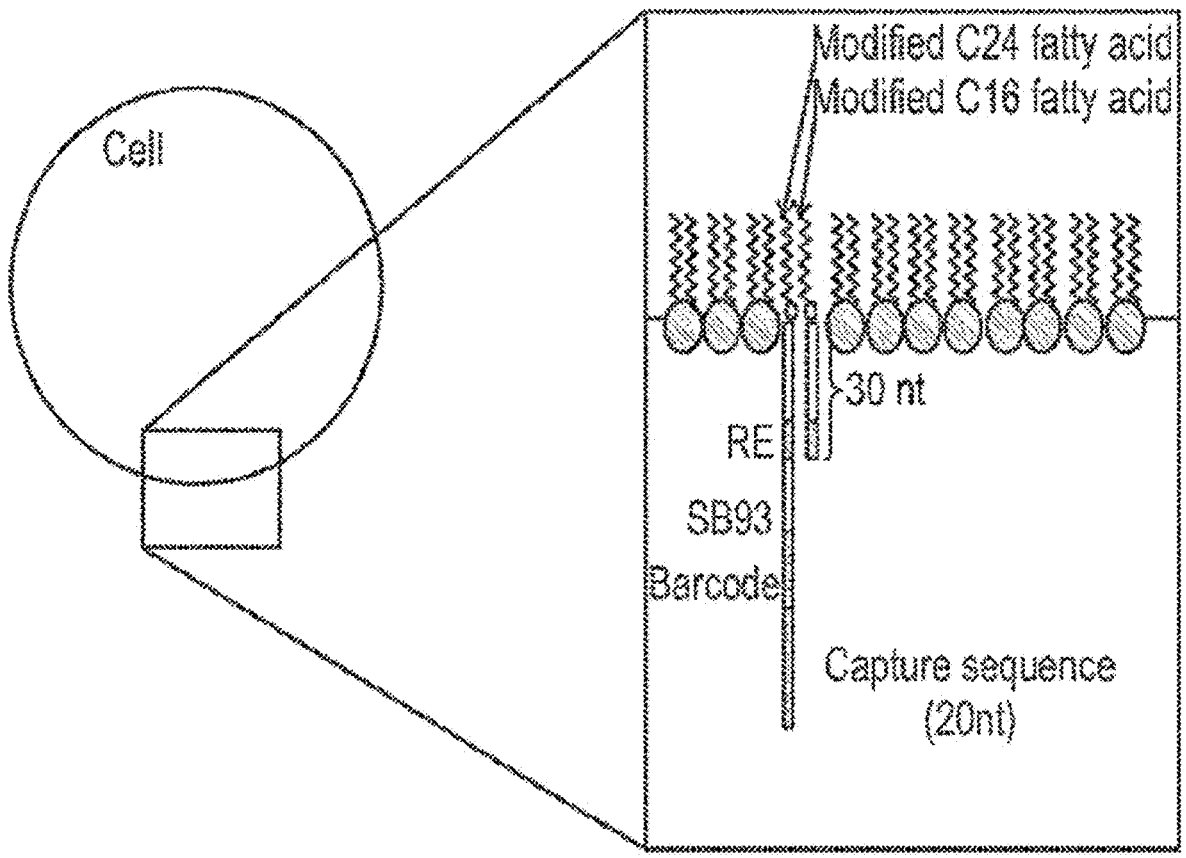

FIG. 9 shows cells tagged by attachment of a pair of nucleic acids to fatty acids in the cell membrane.

Figure 10:
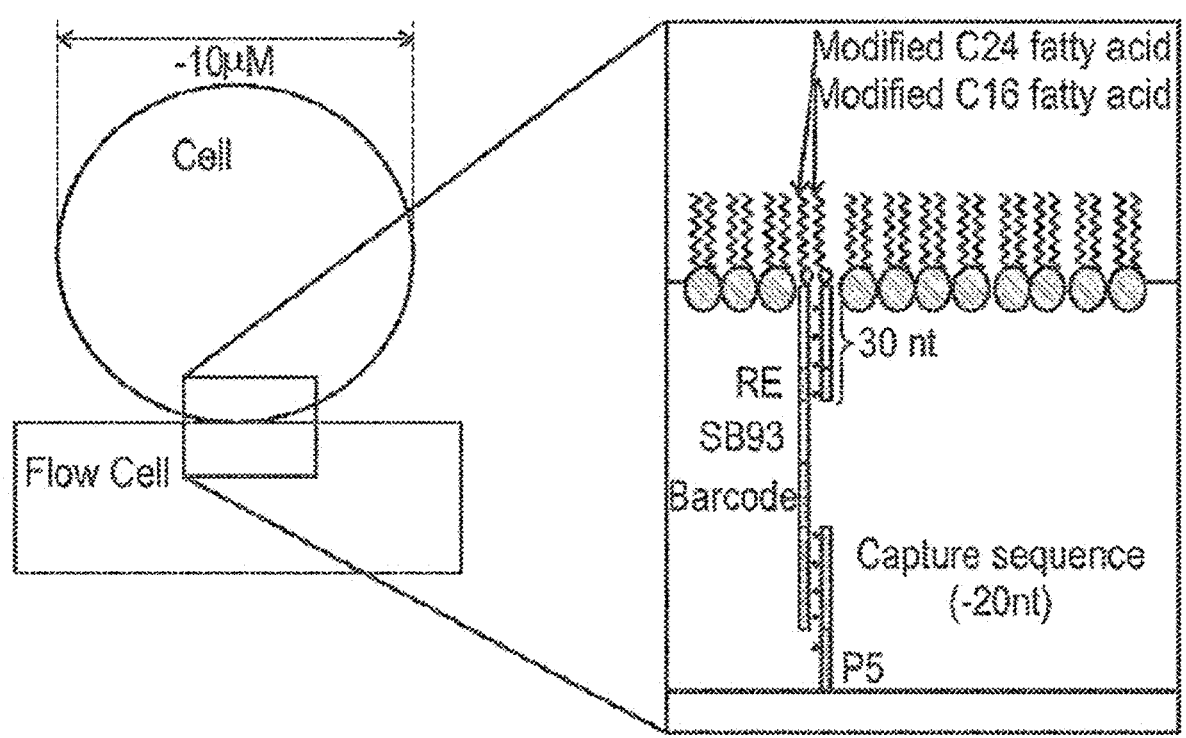

FIG. 10 shows capture of a nucleic acid tagged cell on a flow cell surface.

Figure 11:
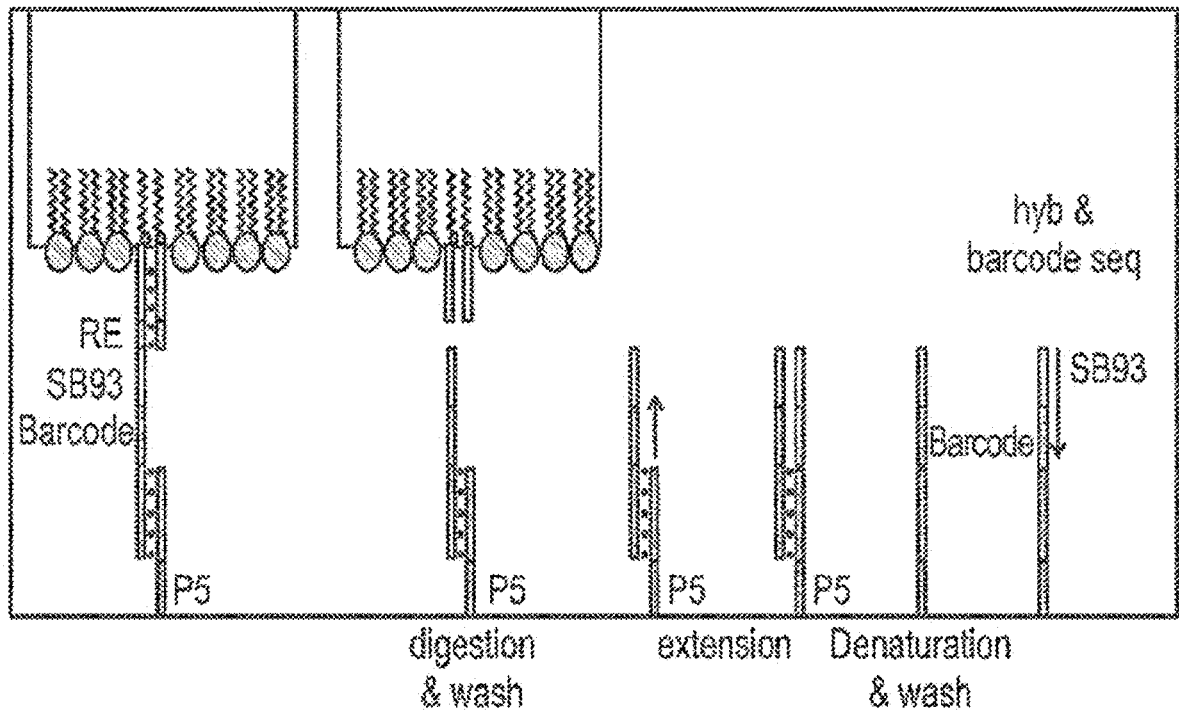

FIG. 11 shows detachment of cells from a flow cell surface via restriction endonuclease cleavage of a nucleic acid tag.

Figure 12:
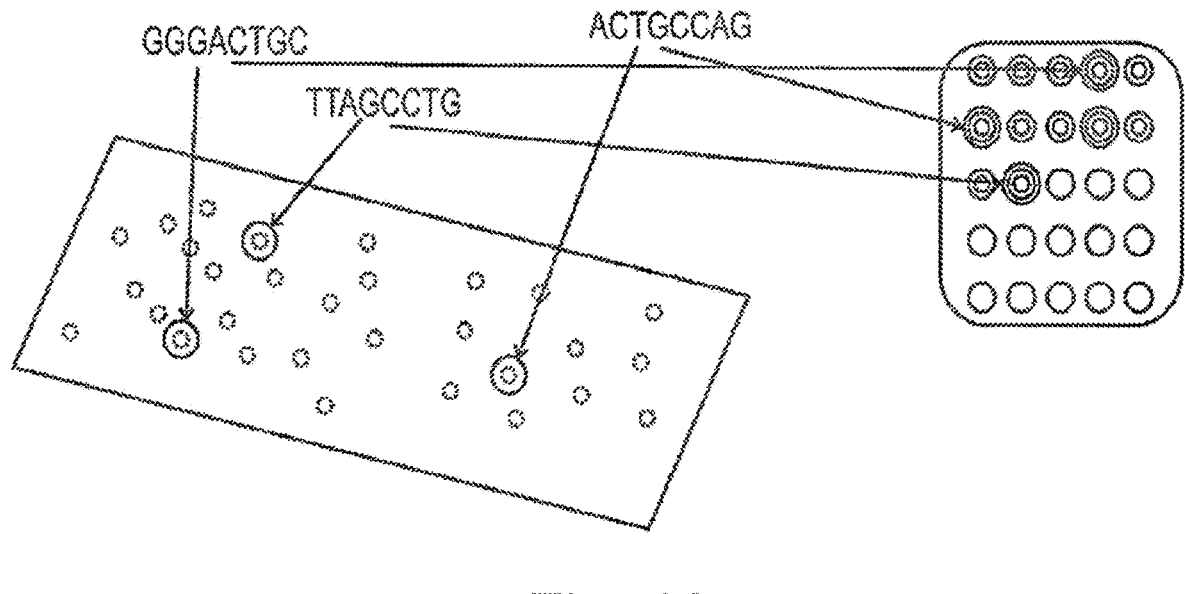

FIG. 12 shows identification of cells on a flow cell surface based on location of decoded tags in vessels from which the cells were obtained.

DETAILED DESCRIPTION

This disclosure provides apparatus and methods for high throughput screening of candidate agents such as candidates for therapeutic use. Particular embodiments set forth herein make beneficial use of nucleic acid sequencing techniques and apparatus. An advantage of using sequencing techniques and apparatus as set forth herein is the ability to spatially array a large number of different candidate agents such that nucleic acids that are associated with each candidate agent can be distinguished and such that the response of each candidate agent to a particular stimulus can be individually detected on the solid support.

In particular embodiments, a plurality of different candidate agents is provided in a library, wherein each candidate agent is attached (or otherwise associated) with a unique nucleic acid tag. The candidate agents can be any of a variety of items including, but not limited to, nucleic acids, proteins, cells and small molecules. These tagged candidate agents can be attached to a solid support such that the individual members form an array of spatially separated candidate agents. Then the array of candidate agents can be screened by exposure to a screening agent (or other stimulus) and reactions of the candidate agent can be detected at spatially resolved locations on the solid support. The location of one or more "hits" can be identified based on spatially resolved detection of an expected, desired or unique signals on the array. A sequencing reaction can also be carried out on the array (either before or after a screen step) in order to identify each tag with respect to its location in the array. A candidate agent can be identified by correlating the location of the "hit" with the identity of the tag at that location.

Some candidate agents used in a method or apparatus set forth herein are nucleic acid-based, including, for example, proteins and cells. In several embodiments that use proteins, sequences of the DNA or RNA molecules that encode the proteins can be determined to distinguish one protein from another. Furthermore, the amino acid sequence of an individual protein can be inferred from the RNA sequence based on the known genetic code. However, in some embodiments neither the proteins nor nucleic acids that encode the proteins need to be sequenced. Rather, each protein can be attached (or otherwise associated) with a tag that has been a priori correlated with the sequence of the protein. Thus, sequencing the tag can be sufficient to distinguish one protein from another. Similarly, cell-based candidate agents contain nucleic acids that can be sequenced to identify individual cells in a population. Furthermore, the nucleic acid sequences can be evaluated to determine useful characteristics of individual cells. Again, the use or a priori assigned tags can allow cell characteristics to be distinguished without the need to sequence other contents of the cell.

Although methods and apparatus of this disclosure are exemplified herein with respect to screening candidate agents for therapeutic function, it will be understood that other functional or structural characteristics can be screened. For example, the methods and apparatus can be used to screen for toxicity, agricultural use (e.g. pesticides, growth factors, hormones etc.), industrial use (e.g. catalysts, dyes, plastics etc.), nutrition (e.g, flavors, preservatives, etc.), environmental cleanup, or the like. Generally, the methods and apparatus can be used to screen for biological or non-biological functions.

The methods and apparatus set forth herein provide an advantage in the ability to make quantitative measurements during high throughput screening. For example, commercially available sequencing platforms, such as those commercialized by Illumina, Inc. (San Diego, CA) include precision optics having a relatively wide dynamic range for quantifying fluorescent signals. A further advantage is the ability to follow temporal dynamics of a screening reaction at multiple locations in an array of candidate agents. In contrast, fluidic sorting methods that are used in many traditional screens provide only a snapshot of a passing candidate agent, thereby confining the measurement to a single time point. The methods and apparatus set forth herein provide high throughput on par or in some cases better than fluidic sorting techniques, but with the added benefit of time based measurements of screening results. A further advantage of the apparatus and methods set forth herein is the ability to detect screen results and to detect tags in a way that allows spatial correlation of tags with screen results in order to identify "hits" from the screen.

Terms used herein will be understood to take on their ordinary meaning in the relevant art unless specified otherwise. Several terms used herein and their meanings are set forth below.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), multiple displacement amplification (MDA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from an amplicon. A subsequent amplicon can have a sequence that is substantially complementary to the target nucleic acid or substantially identical to the target nucleic acid.

As used herein, the term "array" refers to a population of features or sites that can be differentiated from each other according to relative location. Different molecules or other items that are at different sites of an array can be differentiated from each other according to the locations of the sites in the array. An individual site of an array can include one or more molecules (or other items) of a particular type. For example, a site can include a single nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule (or other item). Different items attached to separate substrates can be identified according to the locations of the substrates on a solid support to which the substrates are associated or according to the locations of the substrates in a liquid or gel. Exemplary arrays in which separate substrates are located on a solid support include, without limitation, those having beads in wells.

As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions. In some embodiments attachment can occur via a capture agent. A capture agent can include for example, an antibody, receptor, nucleic acid, ligand, lectin, carbohydrate, avidin, biotin, or analogs thereof As used herein, the term "candidate agent" is intended to mean an item that is suspected to have a particular structure or function. Exemplary items include, but are not limited to molecules, cells and subcellular components. The molecules can optionally be biologically active molecules such as proteins, amino acids, nucleic acids (e.g. DNA or RNA), nucleotides, polysaccharides, saccharides, metabolites, vitamins, enzyme cofactors, or the like. Other candidate agents include macrocycles, cyclic peptides, fused molecules (e.g. nucleic acid-protein fusion), or displayed constructs (e.g. peptides on phage). Exemplary functions that a candidate agent can be suspected of having include, but are not limited to, activation of another agent, inhibition of another agent, chemical modification of another agent, degradation of another agent, synthesis of another agent, wherein the other agent can optionally be any one or more of the items exemplified above as being candidate agents. The structure of a candidate agent can be any known or suspected structure for the above items or other items known in the art.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules. The term can be similarly applied to proteins which are distinguishable as different from each other based on amino acid sequence differences.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "extend," when used in reference to a nucleic acid, is intended to mean addition of at least one nucleotide or oligonucleotide to the nucleic acid. In particular embodiments one or more nucleotides can be added to the 3' end of a nucleic acid, for example, via polymerase catalysis (e.g. DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g. ligase catalysis) methods. A nucleic acid can be extended in a template directed manner, whereby the product of extension is complementary to a template nucleic acid that is hybridized to the nucleic acid that is extended.

As used herein, the term "feature" means a location in an array for a particular species of molecule or cell. A feature can contain only a single molecule (or cell) or it can contain a population of several molecules (or cells) of the same species. In some embodiments, features are present on a solid support prior to attaching a molecule or cell. In other embodiments the feature is created by attachment of a molecule or cell to the solid support. Features of an array are typically discrete. The discrete features can be contiguous or they can have spaces between each other. The size of the features and/or spacing between the features can vary such that arrays can be high density, medium density or lower density. High density arrays are characterized as having sites separated by less than about 15 μm. Medium density arrays have sites separated by about 15 to 30 μm, while low density arrays have sites separated by greater than 30 μm. An array useful herein can have, for example, sites that are separated by less than 100 μm, 50 μm, 10 μm, 5 μm, 1 μm, or 0.5 μm. An apparatus or method of the present disclosure can be used to detect an array at a resolution sufficient to distinguish sites at the above densities or density ranges.

As used herein, the term "flow cell" is intended to mean a vessel having a chamber where a reaction can be carried out, an inlet for delivering reagents to the chamber and an outlet for removing reagents from the chamber. In some embodiments the chamber is configured for detection of the reaction that occurs in the chamber. For example, the chamber can include one or more transparent surfaces allowing optical detection of arrays, optically labeled molecules, or the like in the chamber. Exemplary flow cells include, but are not limited to those used in a nucleic acid sequencing apparatus such as flow cells for the Genome Analyzer®, MiSeq®, NextSeq® or HiSeq® platforms commercialized by Illumina, Inc. (San Diego, CA); or for the SOLID™ or Ion Torrent™ sequencing platform commercialized by Life Technologies (Carlsbad, CA). Exemplary flow cells and methods for their manufacture and use are also described, for example, in WO 2014/142841 A1; U.S. Pat. App. Pub. No. 2010/0111768 A1 and U.S. Pat. No. 8,951,781, each of which is incorporated herein by reference.

As used herein, the term "library" is intended to mean a collection that includes several different items. The items in a collection can differ in structure and/or function. For example, the collection can include nucleic acids having different nucleotide sequences, or the collection can include proteins having different primary structure (i.e. amino acid sequence), secondary structure, tertiary structure or quaternary structure. However, it will be understood that there can be some redundancy of items in a library. For example, multiple copies of a particular nucleic acid or protein can be present in a library that nevertheless includes a large variety of different nucleic acids or proteins. Exemplary types of items that can be in a library include those set forth herein with respect to candidate agents or screening agents.

As used herein, the term "luminescent" means emitting cold body radiation. The term is intended to be distinct from incandescence which is radiation emitted from a material as a result of heat. Generally luminescence results when an energy source displaces an electron of an atom out of its lowest energy ground state into a higher energy excited state; then the electron returns the energy in the form of radiation so it can fall back to its ground state. A particularly useful type of luminescent item is one that emits cold body radiation when energy is provided by excitation radiation. Such items are referred to as "fluorescent" or "photoluminescent". Fluorescence or photoluminescence can be perceived as emission of radiation by an item at a wavelength that is a result of irradiating the item at another wavelength.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art.

As used herein, the term "pitch," when used in reference to features of an array, is intended to refer to the center-to-center spacing for adjacent features. A pattern of features can be characterized in terms of average pitch. The pattern can be ordered such that the coefficient of variation around the average pitch is small or the pattern can be random in which case the coefficient of variation can be relatively large. In either case, the average pitch can be, for example, at least about 10 nm, 0.1 μm, 0.5 μm, 1 μm, 5 μm, 10 μm, 100 μm or more. Alternatively or additionally, the average pitch can be, for example, at most about 100 μm, 10 μm, 5 μm, 1 μm, 0.5 μm 0.1 μm or less. Of course, the average pitch for a particular pattern of features can be between one of the lower values and one of the upper values selected from the ranges above.

As used herein, the terms "protein" or "amino acid" are intended to be consistent with their use in the art and to include naturally occurring species or functional analogs thereof. Naturally occurring proteins generally have a backbone containing peptide bonds. An analog structure can have an alternate backbone linkage including any of a variety of those known in the art. Naturally occurring proteins generally have native amino acids selected from arginine, histidine, lysine, aspartic acid, glutamic acid, serine, threonine, asparagine, glutamine, cysteine glycine, proline, alanine, valine, isoleucine, leucine, methionine, phenylalanine, tyrosine, tryptophan and naturally occurring modifications thereof. Some naturally occurring modifications include phosphorylation (e.g. of serine, threonine, histidine, aspartic acid and glutamic acid), prenylation, isoprenylation, acylation, alkylation, glycosylation, biotinylation, ubiquitination or the like. A protein can include native amino acids having non-natural moieties thereon. A protein can include native or non-native amino acids.

As used herein, the term "react," when used in reference to a first agent and a second agent, is intended to refer to the act of modifying the chemical structure of one or both of the agents, creating one or more covalent bond between the two agents, allowing one of the reagents to catalyze a modification to the chemical structure of the other agent, or specifically binding the two agents (e.g. via non-covalent interactions). Exemplary reactions include, but are not limited to, chemical reactions such as reduction, oxidation, addition, elimination, rearrangement, esterification, amidation, etherification, cyclization, or substitution; binding interactions in which a first agent binds to a second agent with specific affinity; dissociation reactions in which two or more agents detach from each other; fluorescence; luminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding.

As used herein, the term "recombinant" is intended to refer to a non-naturally occurring genetic construct. An example is the product of combining genetic material from more than one origin. Exemplary recombinant molecules include, but are not limited to, DNA, RNA and protein. Origins from which a recombinant molecule can be derived include for example, similar genetic elements from different organisms, different genetic elements from the same organism, different genetic elements from different organisms, synthetic genetic elements, or combinations of synthetic and natural genetic elements.

As used herein, the term "screening agent" is intended to mean an item that has a structure or function that is selective for a first candidate agent compared to a second candidate agent. In many embodiments, the structure or function of the screening agent is known prior to its use in a method or composition of the present disclosure. Exemplary items include, but are not limited to molecules, cells and subcellular components. The molecules can optionally be biologically active molecules such as proteins, amino acids, nucleic acids (e.g. DNA or RNA), nucleotides, polysaccharides, saccharides, metabolites, vitamins, enzyme cofactors, or the like. Exemplary selective functions include, but are not limited to, activation of another agent, inhibition of another agent, chemical modification of another agent, degradation of another agent, synthesis of another agent; wherein the other agent can be any one or more of the items exemplified above as being candidate agents. The structure of a screening agent can be any known or suspected structure for the above items or other items known in the art.

As used herein, reference to "selectively" manipulating (or "selective" manipulation of) a first thing compared to second thing is intended to mean that the manipulation has a greater effect on the first thing compared to the effect on the second thing. The manipulation need not have any effect on the second thing. The manipulation can have an effect on the first thing that is at least 1%, 10%, 50%, 90%, or 99% greater than the effect on the second thing. The manipulation can have an effect on the first thing that is at least 2 fold, 5 fold, 10 fold, 100 fold, $1\times10^3$ fold, $1\times10^4$ fold or $1\times10^6$ fold higher than the effect on the second thing. The manipulation can include, for example, modifying, contacting, treating, changing, cleaving (e.g. of a chemical bond), photo-chemically cleaving (e.g. of a chemical bond), forming (e.g. of a chemical bond), photo-chemically forming (e.g. of a chemical bond), covalently modifying, non-covalently modifying, destroying, photo-ablating, removing, synthesizing, polymerizing, photo-polymerizing, amplifying (e.g. of a nucleic acid), copying (e.g. of a nucleic acid), extending (e.g. of a nucleic acid), ligating (e.g. of a nucleic acid), or other manipulation set forth herein or otherwise known in the art.

As used herein, the term "small molecule" is intended to mean a compound having a molecular weight that is less than approximately 1000 Daltons. In particular embodiments, a small molecule is non-polymeric. However, a small molecule can, in other embodiments, be a dimer or trimer. It will also be understood that a small molecule may be a monomer that is capable of being incorporated into a polymer. Particularly useful small molecule are organic compounds. Useful small molecules can have a molecular weight that is less than 900, 800, 600, 400, 200 or 100 Daltons.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (e.g. acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are components of a flow cell or located within a flow cell apparatus. Exemplary flow cells are set forth in further detail herein.

As used herein, the term "sub-library" is intended to mean a collection having a representation that includes items from a library or copies of items from the library. The representation in the sub-library can be complete or partial by comparison to the representation in the library. A sub-library can be derived by separating at least some of the items from a library or by making copies of at least some of the items in a library.

As used herein, the term "tag sequence" is intended to mean a series of nucleotides in a nucleic acid that can be used to identify or characterize an agent attached to (or associated with) the nucleic acid. The tag sequence can be a naturally occurring sequence or a sequence that does not occur naturally in the organism from which the nucleic acid was obtained. In particular embodiments, one or more tag sequences that are used with a biological sample are not naturally present in the genome, transcriptome or other nucleic acids of the biological sample. For example, tag sequences can have less than 80%, 70%, 60%, 50% or 40% sequence identity to the nucleic acid sequences in a particular biological sample.

As used herein, the term "universal sequence" refers to a series of nucleotides that is common to two or more nucleic acid molecules even if the molecules also have regions of sequence that differ from each other. A universal sequence that is present in different members of a collection of molecules can allow capture of multiple different nucleic acids using a population of universal capture nucleic acids that are complementary to the universal sequence. Similarly, a universal sequence present in different members of a collection of molecules can allow the replication or amplification of multiple different nucleic acids using a population of universal primers that are complementary to the universal sequence. Thus, a universal capture nucleic acid or a universal primer includes a sequence that can hybridize specifically to a universal sequence.

The embodiments set forth below and recited in the claims can be understood in view of the above definitions.

The present disclosure provides a method of characterizing candidate agents. The method can include the steps of (a) providing a library of candidate agents, wherein each candidate agent is attached to a nucleic acid tag having a tag sequence; (b) contacting the library of candidate agents with a solid support to attach the candidate agents to the solid support, whereby an array of candidate agents is formed including individual features on the solid support that each attach to an individual candidate agent from the library; (c) contacting the array of candidate agents with a screening agent, wherein one or more candidate agents in the array react with the screening agent; (d) detecting the array during or after the contacting of the array with the screening agent, thereby determining that at least one candidate agent in the array reacts with the screening agent; (e) sequencing the nucleic acid tags on the array to determine the tag sequence that is attached to each of the candidate agents; and (f) identifying the at least one candidate agent in the array that reacts with the screening agent based on the tag sequence that is attached to the at least one candidate agent.

Any of a variety of candidate agents can be used in a method set forth herein. In some embodiments, candidate agents are selected from the group consisting of proteins, nucleic acids, cells or small molecules. It will be understood that in some embodiments the candidate agents that are used will exclude one or more type of item such as proteins, nucleic acids, cells or small molecules. Examples of these types of items that can be included or excluded from a method or composition are set forth throughout this disclosure.

Useful candidate agents can be molecules having, or suspected of having, biological activity. Exemplary biological activities include, but are not limited to, therapeutic activity, toxicity, hormone activity, activation of biological molecules or cells, inhibition of biological molecules or cells, antibiotic activity, antiviral activity, pesticide activity, effects on an organism or its organs such as psychopharmacological effects or immunological effects, or the like. Particularly useful types of candidate agents are enzyme inhibitors or enzyme activators including, for example, those targeted to enzymes set forth herein. Also useful are candidate activators of cell signaling, or candidate inhibitors of cell signaling. However, in some embodiments the candidate agents need not have, nor be suspected of having, a biological activity. In some cases, a candidate agent will have, or be suspected to have, non-biological activity. Examples of activities that can be non-biological include, without limitation, industrial catalysis, food preservation, petroleum processing, polymer synthesis or the like.

Candidate agents can be polymeric or non-polymeric. Particularly useful polymers include, but are not limited to, proteins, nucleic acids, polysaccharides, protein nucleic acids (PNAs) and plastics. Useful non-polymeric molecules include, for example, lipids, amino acids, nucleotides, enzyme cofactors, metabolites, monosaccharides and other small molecules.

Examples of proteins that are useful as candidate agents include, but are not limited to, antibodies; enzymes such as oxidoreductases, transferases, hydrolases, lyases, isomerases, ligases, kinases, phosphatases, polymerases, proteases, nucleases, cellulases, ligninases, amylases, lipases, mannanases, amylases, glucanases, papain, renin, histone modifying enzymes or esterases; or receptors such as G-coupled receptors, cell surface receptors, immunoreceptors, sensory receptors and nuclear hormone receptors.

Another particularly useful type of candidate agent is a cell, including for example, a cell from an organism including, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a dictyostelium discoideum; a fungi such as *Pneumocystis carinii, Takifugu rubripes*, yeast, Saccharamoyces *cerevisiae* or *Schizosaccharomyces pombe*; or a *Plasmodium falciparum*. Other organisms include a prokaryote such as a bacterium, *Escherichia coli*, staphylococci or *Mycoplasma pneumoniae*; an archae; a virus such as Hepatitis C virus or human immunodeficiency virus; or a viroid. Cells can be derived from a homogeneous culture or population of the above organisms or alternatively from a collection of several different organisms, for example, in a mixed culture, community or ecosystem.

Candidate agents that are used herein can be naturally occurring, for example, being harvested from a native population. For example, candidate agents can be genetically natural cells isolated from a multicellular organism or community. Similarly, proteins, nucleic acids or other biological molecules obtained from one or more genetically natural cell or organism can be used. Alternatively, candidate agents can be synthetic or they can be engineered variants of a naturally occurring agent. For example, genetically engineered cells, proteins or nucleic acids can be used in a method set forth herein. Cells or cellular components used as candidate agents can be derived from single celled organisms or multicellular organisms. In particular embodiments, stem cells, immune cells or biological components derived from one or more of these cells types, can be used as candidate agents herein.

In some embodiments, nucleic acid tags can be synthesized in parallel with the synthesis of the candidate agents. For example, a library of candidate agents can be synthesized using a combinatorial chemistry approach and a specific nucleotide (or sequence of nucleotides) can be added to indicate which of many different chemical moieties is added to each member of the library. Accordingly, the sequence of nucleotides in the tag attached to a particular candidate agent provides a synthesis history for the particular candidate agent, information which can optionally be used to determine the chemical structure of that particular candidate agent. Chemistries used for attachment and combinatorial synthesis methods are described, for example, in U.S. Pat. Nos. 5,565,324; 5,573,905 or 6,060,596, each of which is incorporated herein by reference.

Particular embodiments of the methods set forth herein can include a step of combinatorially synthesizing a library of candidate agents, wherein individual reactions of the combinatorial synthesis that are carried out on each candidate agent are tracked by addition of a unique signature of one or more nucleotides to a nucleic acid tag that is attached to each of the candidate agents, thereby providing a library of candidate agents, wherein each candidate agent is attached to a unique nucleic acid tag.

Nucleic acid tags can be attached to candidate agents using any of a variety of chemistries known in the art appropriate for use with nucleic acids and the particular type of candidate agent in use. In particular embodiments, nucleic acid tags will be covalently attached to candidate agents. In cases where the candidate agent is a nucleic acid or is encoded by a nucleic acid, a continuous nucleic acid can include a tag sequence and a candidate agent sequence. It is also possible to use chemical methods to covalently attach a nucleic acid tag to another nucleic acid that serves as or encodes a candidate agent. Chemistries suitable for attaching a nucleic acid tag to a candidate agent (whether the candidate agent is a nucleic acid or other species) include, for example, N-hydroxysuccinimide esters (NHS esters), imidoesters, hydrazines, carbodiimides, maleimides, haloacetyls, pyridinyl disulfides, diazirines, click chemistry (see e.g. U.S. Pat. Nos. 6,737,236; 7,427,678; 7,375,234; 7,763,736; or 8,129,542, each of which is incorporated herein by reference) or sulfhydrils. Other useful chemistries include those that have been employed to attach nucleic acids to beads or other solid supports as set forth in U.S. Pat. No. 7,259,258 or 7,504,499, each of which is incorporated herein by reference.

Tag sequences can be any of a variety of lengths. Longer sequences can generally accommodate a larger number and variety of tags for a population. Generally, all probes in a plurality will have the same length tag (albeit with different sequences), but it is also possible to use different length tags for different probes. A tag sequence can be at least 2, 4, 6, 8, 10, 12, 15, 20 or more nucleotides in length. Alternatively or additionally, the length of the tag sequence can be at most 20, 15, 12, 10, 8, 6, 4 or fewer nucleotides. Examples of tag sequences that can be used are set forth, for example in, US Pat. App. Publ. No. 2014/0342921 A1 and U.S. Pat. No. 8,460,865, each of which is incorporated herein by reference.

A method of the present disclosure can include a step of contacting a library of candidate agents with a solid support to attach the candidate agents to the solid support. As a result an array of candidate agents can be formed on the support, the array including individual features that each attach to an individual candidate agent from the library.

Any of a variety of solid supports can be used. Particularly useful solid supports are those used for nucleic acid arrays. Examples include glass, modified glass, functionalized glass, inorganic glasses, microspheres (e.g. inert and/or magnetic particles), plastics, polysaccharides, nylon, nitrocellulose, ceramics, resins, silica, silica-based materials, carbon, metals, an optical fiber or optical fiber bundles, polymers and multiwell (e.g. microtiter) plates. Exemplary plastics include acrylics, polystyrene, copolymers of styrene and other materials, polypropylene, polyethylene, polybutylene, polyurethanes and Teflon™. Exemplary silica-based materials include silicon and various forms of modified silicon.

In particular embodiments, a solid support can be within or part of a vessel such as a well, tube, channel, cuvette, Petri plate, bottle or the like. A particularly useful vessel is a flow-cell, for example, as described in WO 2014/142841 A1; U.S. Pat. App. Pub. No. 2010/0111768 A1 and U.S. Pat. No. 8,951,781 or Bentley et al., Nature 456:53-59 (2008), each of which is incorporated herein by reference. Exemplary flow-cells are those that are commercially available from Illumina, Inc. (San Diego, CA) for use with a sequencing platform such as a Genome Analyzer®, MiSeq®, Next-Seq® or HiSeq® platform. Another particularly useful vessel is a well in a multiwell plate or microtiter plate.

Optionally, a solid support can include a gel coating. Attachment of nucleic acids to a solid support via a gel is exemplified by flow cells available commercially from Illumina Inc. (San Diego, CA) or described in US Pat. App. Pub. Nos. 2011/0059865 A1, 2014/0079923 A1, or 2015/0005447 A1; or PCT Publ. No. WO 2008/093098, each of which is incorporated herein by reference. Exemplary gels that can be used in the methods and apparatus set forth herein include, but are not limited to, those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, US Pat. App. Publ. Nos. 2014/0079923 A1, or 2015/0005447 A1, each of which is incorporated herein by reference). A gel can be used to attach candidate agents directly (e.g. via covalent bond between the gel and the candidate agents) or via hybridization of gel attached nucleic acid to complementary nucleic acids that are already attached to the candidate agents.

In some embodiments, a solid support can be configured as an array of features to which nucleic acids and/or candidate agents can be attached. In particular embodiments, each feature will accommodate no more than one candidate agent or will otherwise be configured to contain a single species of a particular mixture of candidate agents. The features can be present in any of a variety of desired formats. For example, the features can be wells, pits, channels, ridges, raised regions, pegs, posts or the like. In some embodiments, the features can contain beads. However, in particular embodiments the features need not contain a bead or particle. Exemplary features include wells that are present in substrates used for commercial sequencing platforms sold by 454 LifeSciences (a subsidiary of Roche, Basel Switzerland) or Ion Torrent (a subsidiary of Life Technologies, Carlsbad California). Other substrates having wells include, for example, etched fiber optics and other substrates described in U.S. Pat. Nos. 6,266,459; 6,355,431; 6,770,441; 6,859,570; 6,210,891; 6,258,568; 6,274,320; US Pat app. Publ. Nos. 2009/0026082 A1; 2009/0127589 A1; 2010/0137143 A1; 2010/0282617 A1 or PCT Publication No. WO 00/63437, each of which is incorporated herein by reference. In some embodiments, wells of a substrate can include gel material (with or without beads) as set forth in US Pat. App. Publ. No. 2014/0243224 A1, which is incorporated herein by reference.

The features on a solid support can be metal features on a non-metallic surface such as glass, plastic or other materials exemplified above. Exemplary solid supports having metal features and methods for their manufacture are provided in U.S. Pat. No. 8,895,249 or US Pat App. Pub. No. 2014/0243224 A1, each of which is incorporated herein by reference.

Features can appear on a solid support as a grid of spots or patches. The features can be located in a repeating pattern or in an irregular, non-repeating pattern. Particularly useful repeating patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features.

High density arrays are characterized as having average pitch (for neighboring features) of less than about 15 μm. Medium density arrays have average pitch of about 15 to 30 μm, while low density arrays have average pitch greater than 30 μm. An array useful in the invention can have average pitch that is less than 100 μm, 50 μm, 10 μm, 5 μm, 1 μm or 0.5 μm. The average pitch values and ranges set forth above or elsewhere herein are intended to be applicable to ordered arrays or random arrays.

In particular embodiments, features on a solid support can each have an area that is larger than about $100 \text{ nm}^2$, $250 \text{ nm}^2$, $500 \text{ nm}^2$, $1 \text{ μm}^2$, $2.5 \text{ μm}^2$, $5 \text{ μm}^2$, $10 \text{ μm}^2$, $100 \text{ μm}^2$, or $500 \text{ μm}^2$ or more. Alternatively or additionally, features can each have an area that is smaller than about $1 \text{ mm}^2$, $500 \text{ μm}^2$, $100 \text{ μm}^2$, $25 \text{ μm}^2$, $10 \text{ μm}^2$, $5 \text{ μm}^2$, $1 \text{ μm}^2$, $500 \text{ nm}^2$, or $100 \text{ nm}^2$ or less. The above ranges can describe the apparent area of a bead or other particle on a solid support when viewed or imaged from above.

In particular embodiments, a solid support can include a collection of beads or other particles. Examples of arrays having beads located on a surface include those wherein beads are located in wells such as a BeadChip™ array (Illumina Inc., San Diego CA), substrates used in sequencing platforms from 454 LifeSciences (a subsidiary of Roche, Basel Switzerland) or substrates used in sequencing platforms from Ion Torrent (a subsidiary of Life Technologies, Carlsbad California). Other solid supports having beads located on a surface are described in U.S. Pat. Nos. 6,266,459; 6,355,431; 6,770,441; 6,859,570; 6,210,891; 6,258,568; or 6,274,320; US Pat. App. Publ. Nos. 2009/0026082 A1; 2009/0127589 A1; 2010/0137143 A1; or 2010/0282617 A1 or PCT Publication No. WO 00/63437, each of which is incorporated herein by reference. Several of the above references describe methods for attaching nucleic acids to beads prior to loading the beads in or on a solid support. As such, the collection of beads can include different beads each having a unique nucleic acid attached. It will however, be understood that the beads can be made to include universal primers, and the beads can then be loaded onto an array, thereby forming universal arrays for use in a method set forth herein. Candidate agents can be attached to beads prior to or after the beads are loaded on a solid support. As set forth previously herein, the solid supports typically used for bead arrays can be used without beads. For example, nucleic acids (such as probes or primers) or candidate agents can be attached directly to the wells or to gel material in wells. Thus, the above references are illustrative of materials, compositions or apparatus that can be modified for use in the methods and compositions set forth herein.

Accordingly, a solid support used in a method set forth herein can include an array of beads, wherein different candidate agents or different nucleic acids are attached to different beads in the array. In this embodiment, each bead can be attached to a different candidate agent or nucleic acid and the beads can be randomly distributed on the solid support in order to effectively attach the different nucleic acids to the solid support. Optionally, the solid support can include wells having dimensions that accommodate no more than a single bead or single candidate agent. In such a configuration, the beads may be attached to the wells due to forces resulting from the fit of the beads in the wells. It is also possible to use attachment chemistries or adhesives to hold the beads in the wells.

A solid support can include, or can be made by the methods set forth herein to attach, a plurality of nucleic acids or candidate agents. For example, a solid support can include at least 10, 100, $1 \times 10^3$, $1 \times 10^4$, $1 \times 10^5$, $1 \times 10^6$, $1 \times 10^7$, $1 \times 10^8$, $1 \times 10^9$ or more different nucleic acids or candidate agents. Alternatively or additionally, a solid support can include at most $1 \times 10^9$, $1 \times 10^8$, $1 \times 10^7$, $1 \times 10^6$, $1 \times 10^5$, $1 \times 10^4$, $1 \times 10^3$, 100, 10 or fewer different nucleic acids or candidate agents. It will be understood that each of the different nucleic acids or candidate agents can be present in several copies, for example, when nucleic acid components of candidate agents have been amplified to form a cluster. Thus, the above ranges can describe the number of different candidate agents or nucleic acid clusters on a solid support. It will also be understood that the above ranges can describe the number of different tags, or other sequence elements set forth herein as being unique to particular nucleic acids or candidate agents. Alternatively or additionally, the ranges can describe the number of extended nucleic acids or modified candidate agents created on a solid support using a method set forth herein.

Features, may be present on a solid support prior to contacting the solid support with nucleic acids or candidate agents. For example, in embodiments where nucleic acids or candidate agents are attached to a support via hybridization to primers, the primers can be attached at the features, whereas interstitial areas outside of the features substantially lack any of the primers. Nucleic acids or candidate agents can be captured at preformed features on a solid support, and optionally amplified on the solid support, using methods set forth in U.S. Pat. Nos. 8,895,249, 8,778,849, or US Pat App. Pub. No. 2014/0243224 A1, each of which is incorporated herein by reference.

In some embodiments, features are formed during or after attachment of nucleic acid tags and/or candidate agents to a solid support. For example, a solid support may have a lawn of primers or may otherwise lack features. In this case, a feature can be formed by virtue of attachment of a nucleic acid or candidate agent on the solid support. Optionally, a captured nucleic acid can be amplified on the solid support such that the resulting cluster becomes a feature. Although attachment is exemplified above as capture between a primer and a complementary portion of another nucleic acid, it will be understood that capture moieties other than primers can be present at pre-formed features or as a lawn. Other exemplary capture moieties include, but are not limited to, chemical moieties capable of reacting with a nucleic acid or candidate agent to create a covalent bond or receptors capable of binding non-covalently to a ligand on a nucleic acid or candidate agent.

In particular embodiments, nucleic acid primers will be attached to a solid support. A library of candidate agents, having attached nucleic acid tags, can attach to the solid support via hybridization of the nucleic acid tags to the attached nucleic acid primers. For example, the nucleic acid tags can include a universal primer binding sequence, the nucleic acid primers can include a universal primer sequence, and the candidate agents can attach to the solid support via hybridization of the universal primer binding sequence to the universal primer sequence. As an alternative to universal primers, the solid support can include target specific primers that hybridize to specific tag sequences.

An array of single candidate agents per feature can be formed by attachment of candidate agents to a solid support. Accordingly, one or more features on a solid support can each include a single candidate agent (e.g. a single molecule, single cell or other single item). The features can be configured, in some embodiments, to accommodate no more than a single candidate agent of a particular type. However, whether or not the feature can accommodate more than one candidate agent, the feature may nonetheless include no more than a single candidate agent, no more than b single nucleic acid tag, or no more than both the single candidate agent and the single nucleic acid tag. Alternatively, an individual feature can include a plurality of candidate agents and/or nucleic acid tags. For example, an individual feature can include an ensemble of nucleic acid molecules and/or an ensemble of proteins having the same sequence as each other. In particular embodiments, the ensemble can be produced by amplification from a single nucleic acid template to produce amplicons, for example, as a cluster attached to each feature.

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In some embodiments the amplification can be carried out in solution. Preferably, an amplification technique used in a method of the present disclosure will be carried out on solid phase. In particular, one or more primer species (e.g. universal primers for one or more universal primer binding site present in a nucleic acid tag) that are attached to a solid support and that hybridize to a nucleic acid tag can be extended in an amplification technique. Taking a solid phase PCR embodiment as an example, one or both of the primers used for amplification can be attached to a solid support (e.g. via a gel). Formats that utilize two species of primers attached to a solid support are often referred to as bridge amplification because double stranded amplicons form a bridge-like structure between the two solid support-attached primers that flank the template sequence that has been copied. Exemplary reagents and conditions that can be used for bridge amplification are described, for example, in U.S. Pat. Nos. 5,641,658, 7,115,400, or 8,895,249; or U.S. Pat. Publ. Nos. 2002/0055100 A1, 2004/0096853 A1, 2004/0002090 A1, 2007/0128624 A1 or 2008/0009420 A1, each of which is incorporated herein by reference. Solid-phase PCR amplification can also be carried out with one of the amplification primers attached to a solid support and the second primer in solution. An exemplary format that uses a combination of a solid support attached primer and soluble primer is the format used in emulsion PCR as described, for example, in Dressman et al., Proc. Natl. Acad. Sci. USA 100:8817-8822 (2003), WO 05/010145, or U.S. Pat. App. Publ. Nos. 2005/0130173 A1 or 2005/0064460 A1, each of which is incorporated herein by reference. Emulsion PCR is illustrative of the format and it will be understood that for purposes of the methods set forth herein the use of an emulsion is optional and indeed for several embodiments an emulsion is not used.

RCA techniques can be modified for use in a method of the present disclosure. Exemplary components that can be used in an RCA reaction and principles by which RCA produces amplicons are described, for example, in Lizardi et al., Nat. Genet. 19:225-232 (1998) and US Pat. App. Publ. No. 2007/0099208 A1, each of which is incorporated herein by reference. Primers used for RCA can be in solution or attached to a solid support. The primers can be one or more of the universal primers described herein.

MDA techniques can be modified for use in a method of the present disclosure. Some basic principles and useful conditions for MDA are described, for example, in Dean et al., Proc Natl. Acad. Sci. USA 99:5261-66 (2002); Lage et al., Genome Research 13:294-307 (2003); Walker et al., Molecular Methods for Virus Detection, Academic Press, Inc., 1995; Walker et al., Nucl. Acids Res. 20:1691-96 (1992); U.S. Pat. Nos. 5,455,166; 5,130,238; and 6,214,587, each of which is incorporated herein by reference. Primers used for MDA can be in solution or attached to a solid support at an amplification site. Again, the primers can be one or more of the universal primers described herein.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a solid support (e.g. universal primers). In this example, amplicons produced after the combined RCA and MDA steps will be attached to the solid support.

A method of the present disclosure can include a step of contacting an array of candidate agents with a screening agent or stimulus. One or more candidate agents in the array may optionally react with the screening agent or respond to the stimulus. As a result, the one or more candidate agents can be classified as hits.

In some embodiments, a screening agent will react with one or more candidate agents in an array by binding to the one or more candidate agents or by blocking binding between the candidate agent and an analyte having affinity for the candidate agent. The array can be detected to identify features where the screening agent is bound. For example, the screening agent can produce a signal that is detectable, for example, due to a label being present on the screening agent.

In some embodiments, a screening agent will modify one or more features on an array where a candidate agent resides. For example, a screening agent can react with a candidate agent by chemically modifying the candidate agent, the screening agent or both. An array can be detected to identify features where modifications have been made. In particular, the modification can produce a signal that is detectable, for example, due to a label being attached to a feature where a candidate agent resides. Exemplary modifications include addition of a label moiety to a feature where a candidate agent resides; addition of an affinity moiety to a feature where a candidate agent resides, wherein the affinity moiety binds to a label; removal of a fluorescent quencher at a feature where a candidate agent resides, wherein a luminescent signal arises due to removal of the quencher; addition of a Forster resonance energy transfer (FRET) donor or acceptor moiety to a feature where a candidate agent resides, wherein the addition alters the apparent luminescence wavelength emitted from the feature; removal of a label moiety from a feature where a candidate agent resides; removal of an affinity moiety from a feature where a candidate agent resides, wherein the affinity moiety binds to a label; removal of a Forster resonance energy transfer (FRET) donor or acceptor moiety from a feature where a candidate agent resides, wherein the removal alters the apparent luminescence wavelength emitted from the feature, or the like.

In some embodiments, a screening agent will react with one or more candidate agents in an array to produce an analyte. An array can be detected to identify features where an analyte has been produced. For example, the analyte can produce a signal that is detectable. Exemplary analytes that can be produced include a luminescent label, a ligand for a detectable receptor, a substrate used by an enzyme to produce a detectable product, or the like.

In some embodiments, a screening agent need not be in direct contact with a library of candidate agents. Rather, a capture agent can be contacted with the screening agent to yield a capture product and then the capture product can be contacted with a collection of candidate agents. In another embodiment, a capture agent can be contacted with a collection of candidate agents to yield a capture product and then the capture product can be contacted with a screening agent. As exemplified by embodiments that use a capture product, a screening agent need not make direct contact with a candidate agent in order for the screening agent to be useful for indicating a desired or suspected structure or function for a candidate agent.

A method set forth herein can further include a step of detecting an array of candidate agents during or after contacting the array with a screening agent, thereby determining that at least one candidate agent in the array reacts with the screening agent. The solid support to which the array is attached can be in any of a variety of states set forth herein. For example, the solid support can include candidate agents along with nucleic acid tags that are attached thereto. Alternatively, the solid support may not include nucleic acid tags, instead being in a state that follows removal of nucleic acid tags from the candidate agents. Nucleic acids (e.g. tags and/or nucleic acid-based candidate agents) can be in single molecule form or ensemble form during a detection step. In still further embodiments, the solid support may not include candidate agents, instead being in a state that follows removal of candidate agents. Accordingly, detection can occur at any of a variety of points in a method set forth herein.

Any of a variety of signals can be detected in a screening step set forth herein including, for example, an optical signal such as absorbance of radiation, luminescence emission, luminescence lifetime, luminescence polarization, or the like; Rayleigh and/or Mie scattering; magnetic properties; electrical properties; charge; mass; radioactivity or the like. Exemplary labels that can be detected in a method set forth herein include, without limitation, a fluorophore, luminophore, chromophore, nanoparticle (e.g., gold, silver, carbon nanotubes), heavy atom, radioactive isotope, mass label, charge label, spin label, receptor, ligand, or the like.

Particular embodiments use imaging techniques. An image can be obtained using detection devices known in the art. Examples include microscopes configured for light, bright field, dark field, phase contrast, fluorescence, reflection, interference, or confocal imaging. In particular embodiments, a fluorescence microscope (e.g. a confocal fluorescent microscope) can be used to detect a screening agent (or other analyte) that is fluorescent, for example, by virtue of a fluorescent label. Fluorescent specimens can also be imaged using a nucleic acid sequencing device having optics for fluorescent detection such as a Genome Analyzer®, MiSeq®, NextSeq® or HiSeq® platform device commercialized by Illumina, Inc. (San Diego, CA); or a SOLID™ sequencing platform commercialized by Life Technologies (Carlsbad, CA). Other imaging optics that can be used include those that are found in the detection devices described in Bentley et al., *Nature* 456:53-59 (2008), PCT Publ. Nos. WO 91/06678, WO 04/018497 or WO 07/123744; U.S. Pat. Nos. 7,057,026, 7,329,492, 7,211,414, 7,315,019 or 7,405,281, and US Pat. App. Publ. No. 2008/0108082, each of which is incorporated herein by reference.

An image of a solid support can be obtained at a desired resolution, for example, to distinguish candidate agents in an array on the solid support. Accordingly, the resolution can be sufficient to distinguish features of an array that are separated by at least 0.5 µm, 1 µm, 5 µm, 10 µm, 50 µm, 100 µm, 500 µm, 1 mm or more. Alternatively or additionally, the resolution can be set to distinguish features of an array that are separated by at most 1 mm, 500 µm, 100 µm, 50 µm, 10 µm, 5 µm, 1 µm, 0.5 µm or less.

A method of the present disclosure can include a step of sequencing a nucleic acid tag to determine the tag sequence that is attached to candidate agents on a solid support (e.g. array). In many embodiments the candidate agents are randomly located in an array and the sequencing reaction provides information to locate each of the different candidate agents. Sequencing can be carried out on the solid support to which a candidate agent and its nucleic acid tag are attached. Thus, a nucleic acid tag need not be removed from the solid support in order to determine its sequence. In some cases candidate agents can optionally be removed from a solid support prior to performing a sequencing reaction on the nucleic acid tag.

In some embodiments the candidate agent is a nucleic acid or is attached to a nucleic acid that encodes the candidate agent. In such embodiments, a sequencing technique can be used to determine the sequence of the candidate agent. Sequencing can be carried out on the solid support to which the candidate agent is attached. A candidate agent and its nucleic acid tag can be sequenced together (e.g. in a continuous sequencing read) or separately (e.g. a non-sequencing step can be carried out between the sequencing of the tag and the sequencing of the candidate agent).

A method of the present disclosure can employ time based detection or kinetic measurements of an array of candidate agents. Thus, detecting of an array can include acquiring signals at several time points for one or more of the individual features on the array. Any of a variety of the signals and labels set forth herein can be detected in a time based or kinetic analysis.

A method of the present disclosure can include a step of sequencing a nucleic acid tag to determine the tag sequence that is attached to a candidate agent in an array. In some embodiments, the candidate agent is a nucleic acid, the candidate agent is encoded by a nucleic acid to which it is attached (e.g. a protein candidate agent attached to an mRNA or cDNA) or the candidate agent contains a nucleic acid (e.g. a cell that contains nucleic acids). Sequencing techniques, such as sequencing-by-synthesis (SBS) techniques, are a particularly useful method.

SBS can be carried out as follows. To initiate a first SBS cycle, one or more labeled nucleotides, DNA polymerase, SBS primers etc., can be contacted with one or more features on a solid support (e.g. feature(s) where nucleic acids are attached to the solid support). Those features where SBS primer extension causes a labeled nucleotide to be incorporated can be detected. Optionally, the nucleotides can include a reversible termination moiety that terminates further primer extension once a nucleotide has been added to the SBS primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the solid support (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with a composition, apparatus or method of the present disclosure are described, for example, in Bentley et al., *Nature* 456:53-59 (2008), PCT Publ. Nos. WO 91/06678, WO 04/018497 or WO 07/123744; U.S. Pat. Nos. 7,057,026, 7,329,492, 7,211,414, 7,315,019 or 7,405,281, and US Pat. App. Publ. No. 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242 (1), 84-9 (1996); *Ronaghi, Genome Res.* 11 (1), 3-11 (2001); Ronaghi et al. *Science* 281 (5375), 363 (1998); or U.S. Pat. Nos. 6,210,891, 6,258,568 or 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to apparatus, compositions or methods of the present disclosure are described, for example, in PCT Pat. App. Publ. No. WO2012/058096, US Pat. App. Publ. No. 2005/0191698 A1, or U.S. Pat. Nos. 7,595,883 or 7,244,559, each of which is incorporated herein by reference.

Sequencing-by-ligation reactions are also useful including, for example, those described in Shendure et al. *Science* 309:1728-1732 (2005); or U.S. Pat. Nos. 5,599,675 or 5,750,341, each of which is incorporated herein by reference. Some embodiments can include sequencing-by-hybridization procedures as described, for example, in Bains et al., *Journal of Theoretical* Biology 135 (3), 303-7 (1988); Drmanac et al., *Nature Biotechnology* 16, 54-58 (1998); Fodor et al., *Science* 251 (4995), 767-773 (1995); or PCT Pat. App. Publ. No. WO 1989/10977, each of which is incorporated herein by reference. In both sequencing-by-ligation and sequencing-by-hybridization procedures, nucleic acids that are present at sites of an array are subjected to repeated cycles of oligonucleotide delivery and detection. Compositions, apparatus or methods set forth herein or in references cited herein can be readily adapted for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some sequencing embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero-mode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), each of which is incorporated herein by reference.

Some sequencing embodiments include detection of a proton released upon incorporation of a nucleotide into an extension product. For example, sequencing based on detection of released protons can use an electrical detector and associated techniques that are commercially available from Ion Torrent (Guilford, CT, a Thermo Fisher subsidiary) or sequencing methods and systems described in US Pat app. Publ. Nos. 2009/0026082 A1; 2009/0127589 A1; 2010/0137143 A1; or US 2010/0282617 A1, each of which is incorporated herein by reference.

A method of the present disclosure can further include a step of removing one or more candidate agents from a solid support. In particular embodiments, candidate agents can be removed from a feature of an array prior to sequencing a nucleic acid tag at the feature. This can be beneficial when the candidate agent interferes with the sequencing technique or when it is desired to protect the candidate agent from reagents used in the sequencing technique. In some embodiments, one or more candidate agents that have been identified as hits in a screen can be selectively removed from an array.

In some embodiments, a candidate agent can be removed by cleaving a tether that attaches it to a solid support. For example, a candidate agent may be tethered to a solid support via a nucleic acid tag to which it is attached. In cases where the tag nucleic acid is attached to the support by hybridization to a complementary nucleic acid, removal can be achieved by denaturing the hybrid complex. Alternatively, the nucleic acid tag can include a cleavage site located between the attachment point to the candidate agent and the tag sequence. As such, the candidate agent can be separated from the tag sequence by a cleavage reaction targeted to the cleavage site. In some methods, a cleavage site can be introduced into a nucleic acid during an amplification or modification step. For example a cleavage site can be introduced into an extended primer during the extension step.

Exemplary cleavage sites include, but are not limited to, moieties that are susceptible to a chemical, enzymatic or physical process that results in bond breakage. For example, the location can be a nucleotide sequence that is recognized by an endonuclease. Suitable endonucleases and their recognition sequences are well known in the art and in many cases are even commercially available (e.g. from New England Biolabs, Beverley MA; ThermoFisher, Waltham, MA or Sigma Aldrich, St. Louis MO). A particularly useful endonuclease will break a bond in a nucleic acid strand at a site that is 3'-remote to its binding site in the nucleic acid, examples of which include Type II or Type IIs restriction endonucleases.

A photo-labile moiety provides a useful cleavage site. Exemplary photo-labile moieties include, but are not limited to (1-(4,5-dimethoxy-2-nitrophenyl)ethyl) ester (i.e. DMNPE) and (1-(2-nitrophenyl)ethyl) ester (i.e. NPE). See *Meth. Enzymol.* 291:307-347 (1998), which is incorporated herein by reference. Other photo-labile moieties, and methods for their synthesis and use, are described in WO 91/06678 or US Pat. Appl. Publ. No. 20100092957 A1, each of which is incorporated herein by reference. A photo-labile moiety can be advantageously used for targeted cleavage of candidate agent from an individual feature. Spatially resolved radiation (e.g. from a laser, focused light source and/or spatial filter/mask) can be used to address an individual feature where a particular candidate agent is tethered via a photo-labile moiety. As a result that particular candidate agent can be selectively removed (compared to candidate agents at other features on the same array).

In some embodiments, a cleavage site is an abasic site or a nucleotide that has a base that is susceptible to being removed to create an abasic site. Examples of nucleotides that are susceptible to being removed to form an abasic site include uracil and 8-oxo-guanine. In a particular embodiment, the USER™ reagent available from New England Biolabs is used. Other examples of cleavage sites and methods that can be used to cleave nucleic acids are set forth, for example, in U.S. Pat. No. 7,960,120, which is incorporated herein by reference.

This disclosure further provides a method for producing an array of proteins. The method can include steps of (a) providing a library of cDNA molecules that are attached to a solid support; (b) amplifying the cDNA molecules on the solid support to form clusters, wherein each cluster includes multiple copies of a particular cDNA molecule from the library; (c) transcribing the multiple copies at the clusters to produce multiple mRNA molecules attached to each of the clusters; and (d) translating the mRNA molecules at the clusters to produce multiple proteins attached to each of the clusters.

This disclosure also provides a method for producing an array of proteins that includes steps of (a) providing a library of mRNA molecules, wherein individual mRNA molecules in the library include a target sequence and a tag sequence, (b) deriving a first sub-library from the library, the first sub-library including nucleic acids having the tag sequences or complements thereof, wherein the nucleic acids are attached to individual features on a solid support, (c) deriving a second sub-library from the library, the second sub-library including nucleic acids having the target sequences and the tag sequences or complements thereof; (d) contacting the second sub-library with the first sub-library, thereby attaching nucleic acids of the second sub-library to the solid support via hybridization of the tag sequences and the complements thereof; and (e) translating the target sequences on the solid support to produce an array of proteins attached to the individual features.

A library of genomic DNA (gDNA), messenger RNA (mRNA) or copy DNA (cDNA) molecules can be derived from one or more organisms that express one or more proteins of interest. For example, the library can be obtained from an organism that is suspected of expressing a desired protein or a protein with a desired activity. Any organism known in the art such as those set forth herein can be used. The organism can be of industrial, therapeutic, diagnostic or prognostic interest. For example, a library can be obtained from a human organism and screened for a prognostic or diagnostic purpose. Alternatively, the organism may be suspected of expressing a gene that produces a therapeutic effect or that has an industrial application. In some embodiments, a library is obtained from a non-human organism or is otherwise non-human in origin.

In some applications, a library of gDNA, mRNA or cDNA molecules includes variants of a single gene that are expressed in a library of recombinant organisms. Such variants can be produced using known protein engineering techniques including, but not limited to those set forth in Sambrook et al., *Molecular Cloning: A Laboratory Manual*, Third Ed., Cold Spring Harbor Laboratory, New York (2001) and in Ausubel et al., *Current Protocols in Molecular Biology*, John Wiley and Sons, Baltimore, Md. (1999), each of which is incorporated herein by reference. For example, the variants can be produced by random mutagenesis of all or part of the gene. Semi-random mutagenesis techniques can also be used.

The genes that are expressed (e.g. as mRNA, cDNA or protein) in a method set forth herein can be selected from the group consisting of antibodies, enzymes, receptors, kinases, phosphatases, polymerases, proteases, esterases, nuclear hormone receptors, histone modifying enzymes and others exemplified herein. The genes can be recombinant, for example, being expressed in an organism that is different from the natural source of the gene or having modifications that are not natural to the gene. In particular embodiments, a gDNA, mRNA, cDNA or protein library can be isolated from a bacteria, yeast, insect, mammalian or other cellular system that is commonly used for cloning or expression.

A library of different nucleic acids (e.g. gDNA, mRNA or cDNA) can be constructed such that each individual member of the library includes a protein coding sequence and a tag sequence. The tag sequence can be assigned to each protein coding sequence randomly or systematically (i.e. where a known tag is a priori associated with a known variant). As an example, tags can be randomly assigned by incorporating random nucleotides into one or more position in the tag region when synthesizing the nucleic acid construct that will also encode the protein. In another example, a population of different nucleic acid tags can be randomly ligated to a population of different protein encoding nucleic acids such that on average each protein encoding nucleic acid will ligate to a unique tag sequence. As an example of systematic tagging, a specific tag can be synthesized into a nucleic acid construct in a way that it is a priori correlated with a mutation or variant in the protein encoding sequence that is in the construct.

A method set forth herein can include a step of deriving a first and second sub-library from a library. In some embodiments, the sub-libraries are derived by removing fractions from a library or by physically splitting the library. Generally, a library will be a fluid that includes multiple copies of each candidate agent. Any of a variety of candidate agents can be used such as gDNA, mRNA, cDNA, macro-cycles, cyclic peptides, fused molecules (e.g. nucleic acid-protein fusion), displayed constructs (e.g. peptides on phage) or protein or the like. As such the sub-libraries that are derived by fractionating or splitting the fluid will be expected to have roughly the same content. In some cases, an amplification step can be carried out on a nucleic acid library (e.g. DNA or RNA library) in order to create the multiple copies.

A gDNA, mRNA, cDNA or protein library can be attached to a solid support using methods set forth elsewhere herein. In a particular embodiment, a library of mRNA molecules is used, wherein each of the mRNA molecules includes a sequence that encodes a candidate agent along with a tag sequence. A first sub-library is derived by a method that includes contacting mRNA molecules of the library with the solid support to attach the mRNA molecules to the solid support. For example, the solid support can have solid support-attached nucleic acid primers and the mRNA molecules can attach to the solid support via hybridization to the nucleic acid primers. By way of more specific example, the mRNA molecules can include a universal primer binding sequence, the nucleic acid primers an include a universal primer sequence, and the mRNA molecules can attach to the solid support via hybridization of the universal primer binding sequence to the universal primer sequence. The attached mRNA molecules can then be copied or amplified on the solid support to produce complements of the tag sequences. Then a second sub-library that is derived from the same library as the first sub-library can be contacted with the amplicons (or copies) of the first sub-library, thereby attaching nucleic acids of the second sub-library to the solid support via hybridization of the tag sequences and the complements thereof. In this way the solid support has been modified to include a library of mRNA molecules that is available for a screening reaction or for translation to produce a library of proteins expressed by the mRNA molecules of the second sub-library.

In some embodiments, one of the first nucleic acid or second nucleic acid sub-libraries can be copied or amplified in solution. As such the amplified or copied sub-library will include complementary tag sequences that can be hybridized to tag sequences in the other sub-library. Either of the sub-libraries can be attached to the solid support and the other sub-library can be hybridized to create a solid support having a library of nucleic acid molecules that is available for a screening reaction, transcription reaction to produce mRNA and/or translation reaction to produce a library of proteins.

For embodiments that utilize an mRNA library, a first sub-library can be derived by a method that includes reverse transcribing some or all of the individual mRNA molecules in the library to produce cDNA. The reverse transcription can occur in solution or on a solid support. The resulting cDNA molecules can then be amplified in solution or on the solid support. Thus, cDNA molecules can be produced having complements of the tag sequences that were in the library. In some cases, the cDNA molecules can include no more than a portion of the mRNA molecules, for example, a portion that expresses a particular domain or a subset of domains from a multidomain protein.

A method of the invention can include a step of transcribing cDNA to mRNA. Transcription can be carried out using known cocktails such as those set forth in Sambrook et al., *Molecular Cloning: A Laboratory Manual*, Third Ed., Cold Spring Harbor Laboratory, New York (2001) and in Ansubel et al., *Current Protocols in Molecular Biology*, John Wiley and Sons, Baltimore, Md. (1999), each of which is incorporated herein by reference, or those that are commercially available. In particular embodiments, transcription is carried out on support-attached cDNA molecules. The mRNA products of the transcription reaction can be attached at the features where they are produced. For example, attachment can be achieved using techniques set forth in Example II, herein. It can also be useful to attach proteins to DNA molecules that encode them (e.g. by direct attachment or co-localization in emulsion droplets). Proteins can also be attached in proximity to DNA molecules that encode them (e.g. a nucleic acid programmable protein array (NAPPA)).

A method of the invention can include a step of translating mRNA to protein. Translation can be carried out using known cocktails such as those set forth in Sambrook et al., *Molecular Cloning: A Laboratory Manual*, Third Ed., Cold Spring Harbor Laboratory, New York (2001) and in Ausubel et al., *Current Protocols in Molecular Biology*, John Wiley and Sons, Baltimore, Md. (1999), each of which is incorporated herein by reference, or those that are commercially available. In particular embodiments, translation is carried out on support-attached mRNA molecules. The protein products of the translation reaction can be attached at the features where they are produced. For example, attachment can be achieved using techniques set forth in Example II, herein.

The methods set forth herein for producing an array of proteins can be put to use in a method of screening proteins. The method can include steps of (i) producing the array of proteins; (ii) contacting the array of proteins with a screening agent, wherein one or more proteins in the array react with the screening agent (or stimulus); and (iii) detecting the array of proteins during or after the contacting with the screening agent (or stimulus), thereby determining that at least one protein in the array reacts with the screening agent (or stimulus).

In particular embodiments, the screening agent reacts with the one or more proteins by binding to the one or more proteins or by blocking binding between a protein and an analyte having affinity for the protein. The detecting of the array can include detecting the screening agent that is bound to the one or more proteins. For example, the screening agent can be luminescent and the detecting can be carried out by detecting luminescence on the array.

In some embodiments, the screening agent reacts with the one or more proteins by chemically modifying the one or more proteins. In this case the detecting of the array can be achieved by detecting the one or more modified proteins. For example, the one or more modified proteins can be luminescent and the detecting can be achieved by detecting luminescence on the array.

In some embodiments, the screening agent reacts with the one or more proteins by producing an analyte product. In this case, the detecting of the array includes detecting the analyte product. For example, the analyte product can be luminescent and the detecting can be carried out by detecting luminescence on the array.

As set forth previously herein, the detecting of the array can include acquiring signals at several time points for one or more of the individual features on the array.

Tag sequences that are part of gDNA, cDNA or mRNA molecules can be sequenced using methods set forth herein or known in the art. For example a sequencing reaction can be carried out on the solid support where a screen is, was, or will be carried out. Thus, a method set forth herein can include a step of sequencing tag sequences, or complements thereof, on the solid support, thereby determining locations of the tag sequences, or complements thereof, at the individual features on the solid support. Such methods can further include a step of identifying at least one protein in the array that reacts with a screening agent based on the tag sequence that is attached to the at least one protein.

A method set forth herein can further include a step of sequencing the candidate gDNA, cDNA or mRNA on the solid support. Thus, one or more sequencing reactions can be carried out on a solid support to determine the identity of the tag sequence and/or the identity of the candidate sequence, thereby determining locations of desired candidate agents at the individual features on the solid support.

In some cases the gDNA, cDNA or mRNA may be longer than the average read length of the sequencing method. In such cases, the candidate nucleic acids can be subjected to several sequencing runs, each using a different primer. For example, a first sequencing run can use a primer that hybridizes to a universal priming sequence that is commonly employed in sequencing methodologies and platforms set forth herein or in references incorporated herein. A subsequent sequencing run can be carried out using a second sequencing primer that hybridizes downstream of the location where the first sequencing primer had hybridized. The primers can be spaced in accordance with the expected read length of the sequencing run such that overlapping or abutting reads of the template nucleic acid can be obtained. Several sequencing runs can be repeated for a sufficient number of sequencing primers to cover the desired region(s) of the candidate nucleic acid.

Another option when the candidate nucleic acid is longer than the average read length of the sequencing method is to use a cassette approach. In the cassette approach, a small region or domain of the nucleic acid is mutated or modified in the candidate nucleic acids. The cassette can be selected to be short enough to be read in a single sequencing run. So long as the region of the candidate nucleic acid that is upstream of the cassette is uniform in all members of the library, it can effectively serve as a universal priming site and a sequencing primer can hybridize to this region for localized sequencing at the cassette.

In some embodiments the candidate gDNA, cDNA or mRNA need not be sequenced. Rather, the tag sequence may have been a priori associated with a known candidate nucleic acid sequence such that sequencing the tag will be sufficient to identify the candidate nucleic acid. The a priori knowledge of the tag present at a particular feature can be correlated with the signals observed from the feature in a screening step in order to identify the candidate nucleic acid, the protein it encodes or properties of the protein.

In some embodiments, a candidate nucleic acid (e.g. gDNA, cDNA or mRNA) or protein can be removed by cleaving a tether that attaches it to a solid support. For example, such candidate agents may be tethered to a solid support via a tag sequence. A cleavage site can be located between the attachment point to the candidate agent and the tag sequence. As such, the candidate agent can be separated from the tag sequence by a cleavage reaction targeted to the cleavage site. Exemplary cleavage sites include, but are not limited to, those set forth elsewhere herein or otherwise known in the art.

Accordingly, a method of the present disclosure can include a step of selectively removing gDNA, cDNA, mRNA or protein molecules that are attached to one or more features of an array. The selective removal can include light mediated cleavage of a photo-labile bond that attaches the molecules to the features, for example, using reagents and methods set forth elsewhere herein.

This disclosure provides an array that includes (a) a solid support; (b) a library of different cDNA molecules attached to the solid support, wherein each different cDNA molecule is attached to an individual feature on the solid support, and wherein each feature includes multiple copies of a particular cDNA molecule; (c) mRNA molecules attached to the cDNA molecules, wherein each of the cDNA molecules is complementary to the respective attached mRNA molecule; and (d) protein molecules attached to the mRNA molecules, wherein each of the protein molecules is encoded by the respective attached mRNA molecule.

This disclosure further provides an array that includes (a) a library of mRNA molecules, wherein individual mRNA molecules in the library comprise a target sequence and a tag sequence, (b) a solid support comprising nucleic acids having complements of the tag sequences, wherein the nucleic acids are attached to individual features on a solid support, wherein the tag sequences of the individual mRNA molecules are hybridized to respective complementary tag sequences at the individual features on the solid support, and wherein proteins derived by translation of the mRNA molecules are attached to respective mRNA molecules.

An array of the present disclosure can include components resulting from one or more steps of a method set forth herein. For example, nucleic acids, such as gDNA, cDNA or mRNA species, can be attached to a solid support in accordance with methods set forth herein. Similarly, proteins can be attached to a solid support in accordance with methods set forth herein. In particular embodiments, cDNA can be attached to a solid support, the encoded mRNA can be attached to the cDNA, and the encoded protein can be attached to the mRNA, as set forth in Examples II and III. As set forth in those examples, attachment via cDNA is optional and instead the mRNA can be attached to the solid support (e.g. via hybridization to a complementary tag or via other attachment methods), and the encoded protein can be attached to the mRNA.

Optionally, an mRNA molecule can be attached to its encoding cDNA molecule via a complex formed with an RNA polymerase. The attachment can be mediated by covalent crosslinking between the complexed cDNA, mRNA and RNA polymerase. Similarly, a protein molecule can be attached to its encoding mRNA via a complex formed with a ribosome. The attachment can be mediated by covalent crosslinking between the complexed mRNA, protein and ribosome.

Any of a variety of screening agents, labels or products of a screening step set forth herein can be present in an array of the present disclosure. For example, features where proteins are located can be luminescently labeled, optionally, via specific, non-covalent binding of a luminescent molecule (such as a screening agent) to the proteins or via a luminescent moiety attached covalently to the proteins. Not all of the features will necessarily be labelled. Rather, a subset of features that contain proteins having a desired or selected activity can be selectively labelled while other features are not labelled. For example, fewer than 50%, 25%, 10%, 5% or 1% of the features may be labelled depending upon the content of the library and the nature of the screen.

Any of a variety of the candidate agents and/or nucleic acid tags set forth herein can be present in an array of the present disclosure. The number of different species on an array, density of features containing the species on an array or the number of each species attached at a particular feature can be in a range set forth herein in regard to methods for making and using arrays.

Also provided by this disclosure is a method of screening cells. The method can include the steps of (a) providing a plurality of different cells, wherein each of the different cells includes a nucleic acid tag having a tag sequence; (b) contacting a mixture of the different cells with a solid support to form an array of cells attached to the solid support; (c) screening the array of cells on the solid support for at least one optical characteristic, wherein the screening reaction includes detecting the individual cells that are attached to the solid support; (d) sequencing the tag sequences of nucleic acid tags that are attached to the solid support; and (e) identifying at least one cell in the array as a candidate cell based on the optical characteristic and the tag sequence of the candidate cell.

In particular embodiments, cells are used as candidate agents in a method set forth herein. The cells can be natural cells isolated from a multicellular organism, natural cells that comprise single cell organisms, genetically engineered cells from a multicellular organism or genetically engineered single celled organisms. The cells used in a method or composition set forth herein can be obtained from a native source or they can be obtained from an ex vivo culture.

Cells that can be copied, cultured or expanded ex vivo are particularly useful. For example, it can be useful to make one or more copies of a candidate cell prior to or after a screening step. Thus, a cell that is identified as a hit in a screen (or a clone of the cell) can be isolated from a preformed stock or from the solid support used in the screen. The isolated cell can be further used or manipulated, for example, to more fully characterize the cell or to employ the cell in a therapeutic procedure.

For embodiments that employ genetically modified cells, the genetic modification can be any of a variety known in the art including, for example, those that result in expressing a non-native recombinant protein, expressing a mutant recombinant protein, deleting all or part of the coding sequence of a naturally occurring protein, inhibiting expression of a naturally occurring protein, enhancing expression of a naturally occurring protein, producing a non-native analyte or inhibiting production of a native analyte. For example, the coding sequences for one or more genes in a library of candidate cells can contain point mutations, deletions (e.g. removal of the entire protein coding sequence, a domain or other portion of the protein), or insertions (e.g. chimeras).

Candidate cells that are in a library can include nucleic acid tags. Several exemplary methods for tagging cells are set forth in Example IV and/or set forth below.

In some embodiments, nucleic acid tags can be covalently attached to the surface of cells. Generally, methods are employed to tag each cell in a library with only a single nucleic acid tag sequence (although multiple nucleic acid molecules each having a copy of the same tag sequence can be present in or on each cell). For example, cells can be physically isolated such that each cell can be individually reacted with a nucleic acid tag molecule. Methods for physically separating cells include for example, separation of each cell into an individual vessel, well on a microplate, feature on an array, bead, fluidic droplet in a droplet actuator device, fluid droplet in an emulsion, or vesicle.

Particularly useful methods for creating droplets to which nucleic acid tags can be delivered include for example, those commercialized by RainDance Technologies (Billerica, MA) or described in U.S. Pat. Nos. 9,017,623 or 8,857,462, each of which is incorporated herein by reference. Further methods for creating and adding tags to droplets are commercialized by 10× Genomics or described in US Pat. App. Pub. Nos. 2014/0155295 A1; 2014/0206554 A1; 2014/0227684 A1 or 2014/0378322 A1, each of which is incorporated herein by reference. These methods can be modified such that cells (or other candidate agents set forth herein) are loaded into individual droplets and the loaded droplets are interacted with fluids that contain nucleic acid tags such that individual droplets end up with a single tag nucleic acid species and a single candidate agent species. Of course, multiple copies of the nucleic acid species or multiple copies of the candidate agent species can be present in an individual droplet. In some embodiments, the nucleic acid tags are attached to beads that are delivered to the individual droplets. The nucleic acid tags can become attached to the surface of the cells using attachment chemistries set forth herein for example in Example IV.

A particularly useful droplet manipulation device that can be used to separate cells (or other candidate agents), for example, to tag the cells, is a droplet actuator as described for example in U.S. Pat. Nos. 8,637,242, 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," *Lab Chip*, 10:832-836 (2010), each of which is incorporated herein by reference.

In particular embodiments, cells in a library can be genetically modified to include a nucleic acid tag. For example, individual cells in a population can carry a plasmid encoding a tag sequence or the genome of individual cells can be modified to include a tag sequence. In some cases, the tag sequence is encoded in a nucleic acid construct that also includes a genetic variant that is to be screened in a method set forth herein.

A library of different cells can be constructed such that each individual cell acquires a randomly assigned tag sequence or each cell can be modified to include a known tag sequence. For example, random tagging can be carried out by incorporating random nucleotides into one or more positions in a tag region when synthesizing a nucleic acid construct that will also encode a genetic variant to be screened. In another example, a population of different nucleic acid tags can be randomly ligated to a population of different variant encoding nucleic acids such that on average each variant nucleic acid will ligate to a unique tag sequence. The constructs can then be added to cells in a library. Similarly, a population of different nucleic acid tags can be covalently attached to a population of different cells such that on average each cell attach to a unique tag sequence.

In other embodiments, a library of different cells can be constructed such that each individual cell acquires a known tag that is a priori associated with a known cell. As an example of a priori tagging, a specific tag can be synthesized into a nucleic acid construct in a way that it is correlated with a mutation or variant in that construct. In some embodiments, cells are physically separated from each other and nucleic acids with known tag sequences are contacted with the cells to form covalent attachment of a single type of tag with a single cell.

In a particular embodiment, a nucleic acid tag can be attached to a bead and the bead can bind to a cell. Optionally, the bead can be attached to an antibody having specific binding affinity or the cell. However, other attachment modalities can be used to attach beads to cells including, for example, those exemplified herein in the context of attaching nucleic acids to candidate agents or solid supports.

In some embodiments, a nucleic acid tag can be attached to a cell by covalent attachment of the nucleic acid tag to a plasma membrane lipid or fatty acid of the cell. Alternatively, a nucleic acid tag can be attached to a cell by covalent attachment to a protein in a plasma membrane lipid of the cell. As an alternative to covalent attachment, a nucleic acid tag can include a receptor that binds to a ligand on the cell surface or a nucleic acid tag can include a ligand that binds to a receptor on the cell surface. Exemplary attachment methods are set forth in Example IV below.

A library of cells can be attached to an array using one or more of the methods set forth herein for attaching other types of candidate agents to a solid support. For example, a solid support can include nucleic acid primers and the cells can attach to the solid support via hybridization of nucleic acid tags to the nucleic acid primers. In some cases, the nucleic acid tags can include a universal primer binding sequence, the nucleic acid primers can include a universal primer sequence, and the candidate agents can attach to the solid support via hybridization of the universal primer binding sequence to the universal primer sequence.

A method of the present disclosure can include a step of extending solid support-attached primers to which nucleic acids, such as nucleic acid tags, are hybridized. The resulting extended primers will include tag sequences and other sequences from the nucleic acids (albeit in complementary form). The extended primers are thus spatially tagged versions of the nucleic acids from the candidate agents. It will be understood that sequence elements, other than tag sequences, that are present in the nucleic acid can also be included in the extended primers. Such elements include, for example, primer binding sites, cleavage sites, other tag sequences (e.g. sample identification tags), capture sequences, recognition sites for nucleic acid binding proteins or nucleic acid enzymes, or the like.

Extension of primers can be carried out using methods exemplified herein or otherwise known in the art for amplification of nucleic acids or sequencing of nucleic acids. In particular embodiments one or more nucleotides can be added to the 3' end of a primer, for example, via polymerase catalysis (e.g. DNA polymerase, RNA polymerase or reverse transcriptase). Chemical or enzymatic methods can be used to add one or more nucleotide to the 3' or 5' end of a primer. One or more oligonucleotides can be added to the 3' or 5' end of a primer, for example, via chemical or enzymatic (e.g. ligase catalysis) methods. A primer can be extended in a template directed manner, whereby the product of extension is complementary to a template nucleic acid that is hybridized to the primer. In some embodiments, a DNA primer is extended by a reverse transcriptase using an RNA template, thereby producing a cDNA. Thus, an extended probe made in a method set forth herein can be a reverse transcribed DNA molecule. Exemplary methods for extending nucleic acids are set forth in US Pat. App. Publ. No. US 2005/0037393 A1 or U.S. Pat. No. 8,288,103 or 8,486,625, each of which is incorporated herein by reference.

All or part of a nucleic acid that is hybridized to a primer can be copied by extension. For example, an extended probe can include at least, 1, 2, 5, 10, 25, 50, 100, 200, 500, 1000 or more nucleotides that are copied from a nucleic acid. The length of the extension product can be controlled, for example, using reversibly terminated nucleotides in the extension reaction and running a limited number of extension cycles. The cycles can be run as exemplified for SBS techniques and the use of labeled nucleotides is not necessary. Accordingly, an extended primer produced in a method set forth herein can include no more than 1000, 500, 200, 100, 50, 25, 10, 5, 2 or 1 nucleotides that are copied from a nucleic acid. Of course extended probes can be any length within or outside of the ranges set forth above.

A library of cells that is attached to an array can be screened using methods set forth herein with regard to screening other candidate agents. In particular embodiments, the screening of the array of cells can include a step of treating the cells with a screening agent. As a result, the screening agent may bind to at least one candidate cell on the array. Optionally, the screening agent is luminescent and the screening reaction will be carried out by detecting luminescence of the at least one candidate cell.

In some embodiments, a screening agent that is delivered to an array will modify at least one candidate cell in the array. For example, the screening agent may stimulate at least one candidate cell on the array. Alternatively, the screening agent may inhibit or even kill at least one candidate cell on the array A screening agent that is contacted with an array of cells may increase or decrease luminescence of at least one candidate cell and the screening reaction can include steps of detecting luminescence of the at least one candidate cell.

As set forth elsewhere herein, the detection step can include a kinetic or time based measurement. For example, detecting of an array of cells can include a step of acquiring signals at several time points for one or more of the individual features on the array.

Nucleic acid tags that are attached to cells or present in cells can be sequenced in a method set forth herein. Nucleic acids that are attached to cells can be sequenced on the cells. Alternatively, the nucleic acids can be transferred to a solid support, for example, via primer extension methods such as those exemplified in Example IV, and the regions of the extended primers that contain the tag sequence (or complement thereof) can be sequenced on the solid support. Methods set forth elsewhere herein for sequencing solid support-attached nucleic acids can be used for nucleic acid tags that are attached to cells or to features in proximity to the cells from which the nucleic acid tags were derived.

In some cases, it may be desirable to remove cells from the solid support while leaving the nucleic acid tags (or copies of the tags) attached to the solid support. The tag sequences can then be sequenced in the absence of the cells.

For embodiments where nucleic acid tags are present in a cell, the cells may be lysed on the surface of the array leading to release of the cell contents and localized capture of the nucleic acid tags. The nucleic acid tags can include universal sequence regions that are complementary to primers on the solid support. Thus, the nucleic acid tags can be captured on the solid support in a format that is amenable to amplification and/or sequencing. The nucleic acids that are captured on the solid support can optionally be amplified. The nucleic acids that are captured on the solid support or the amplicons produced therefrom can be sequenced on the solid support using methods set forth herein.

A method of the present disclosure can include a step of removing one or more cells from the array. For example, one or more cells that are identified as hits in a screening step can be selectively removed. Optionally, conditions can be used that retain viability of the cells. As such the removed cell(s)

can be cultured, copied or expanded. The cell(s) can be removed using techniques and reagents set forth elsewhere herein for other candidate agents. For example, the use of photo-labile linkers and spatially filtered light beams can be particularly useful for isolating a particular cell from others in the array.

In some embodiments viable cells need not be removed from the array following a screening step. Rather, the tag sequence may have been a priori associated with a known cell such that sequencing the tag will be sufficient to identify the cell without further need to isolate or characterize the cells. The a priori knowledge of the tag present at a particular feature can be correlated with the signals observed from the feature in a screening step in order to identify the cell.

The following examples are intended to illustrate but not limit the present invention.

EXAMPLE I

Small Molecule Screening

Next Generation sequencing platforms, such as those commercialized by Illumina (San Diego, CA), provide a foundation to build an integrated high throughput screening platform for drug discovery. By modifying nucleic acids with a functional group that enables attachment to target molecules, it is possible to utilize a sequencing flow cell as a substrate to build arrays for high throughput compound screening. A variety of screening assays can be implemented using the same platform with changes to the attached targets. An exemplary method for screening small molecules on a sequencing platform is diagrammed in FIG. 1A through FIG. 1F, and described below.

Figure 1A:
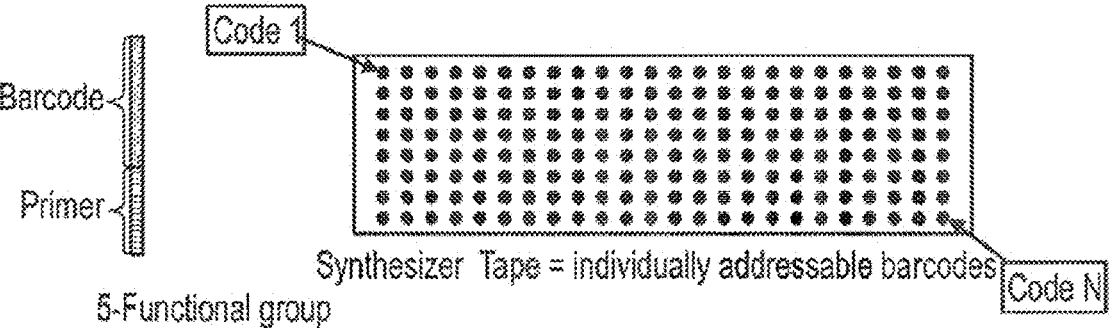
FIG. 1A through FIG. 1F show steps in a process for high throughput screening of candidate agents.

FIG. 1A shows a first step in which 50,000 different nucleic acid molecules, each being 29 nucleotides long, are synthesized on a tape-based synthesis instrument. The tape includes individually addressable sites at which individual nucleic acid species are synthesized, respectively. The nucleic acid molecules also include a functional group (FG) such as a sulfhydryl, amine or N-hydroxysuccinimide group at the 5' end. The 5' region of the nucleic acids include 10 nucleotides that encode a universal primer (that is the same for all of the 50,000 nucleic acids) and the 3' region encodes one of 50,000 different tag sequences (also called "code" sequences). An exemplary tape-based DNA synthesis instrument is described in US Pat. App. Publ. No. 2011/0178285 A1, which is incorporated herein by reference.

Figure 1B:
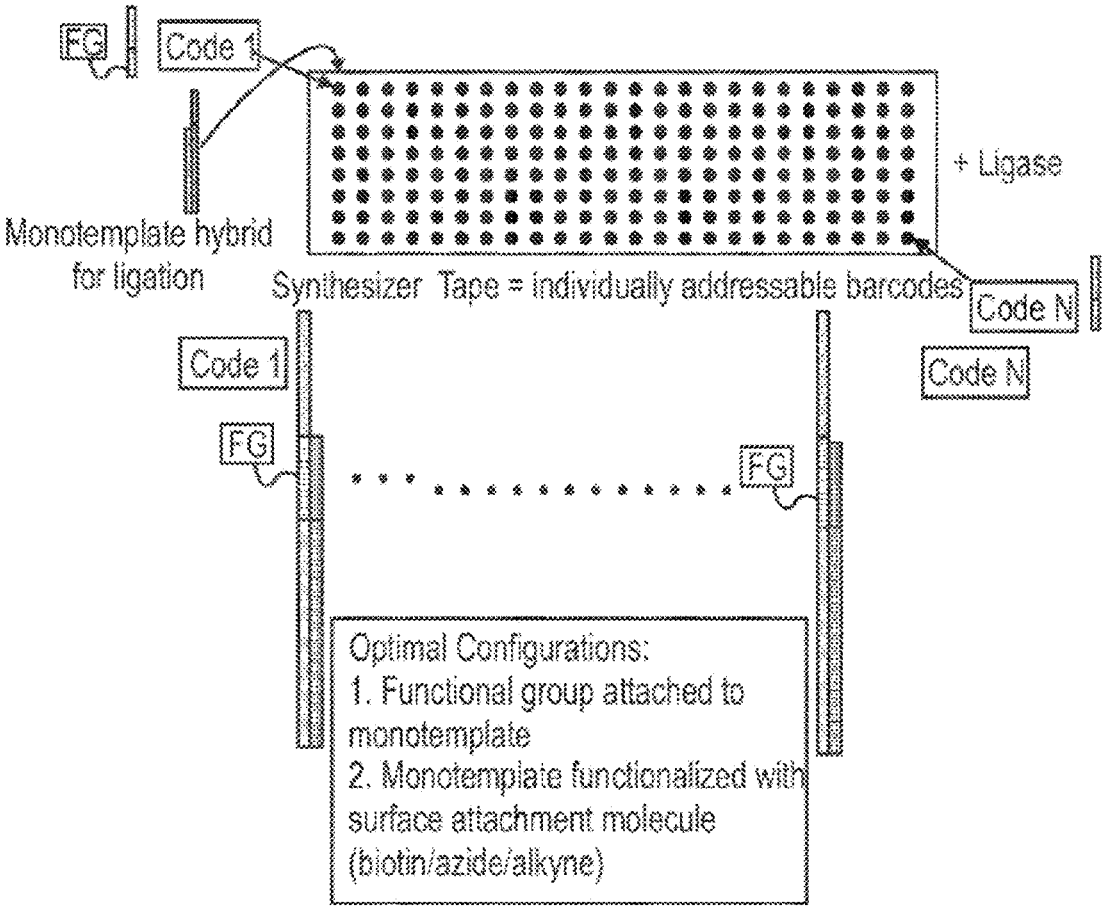

A second step is shown in FIG. 1B, where a monotemplate hybrid nucleic acid is ligated to the nucleic acids in each well of the synthesis tape to create a universal overhang primer. As shown in the diagram, ligation occurs following hybridization of the universal primer sequence of the different nucleic acids with an overhang on the monotemplate hybrid. Optionally, the different nucleic acids can be removed from the tape (e.g. to purify or modify the nucleic acids) prior to the ligation event. Other optional configurations include having the functional group attached to the monotemplate hybrid instead of the different nucleic acids. Alternatively or additionally, the monotemplate hybrid can have a surface attachment moiety such as a biotin, azide or alkyne group.

Figure 1C:
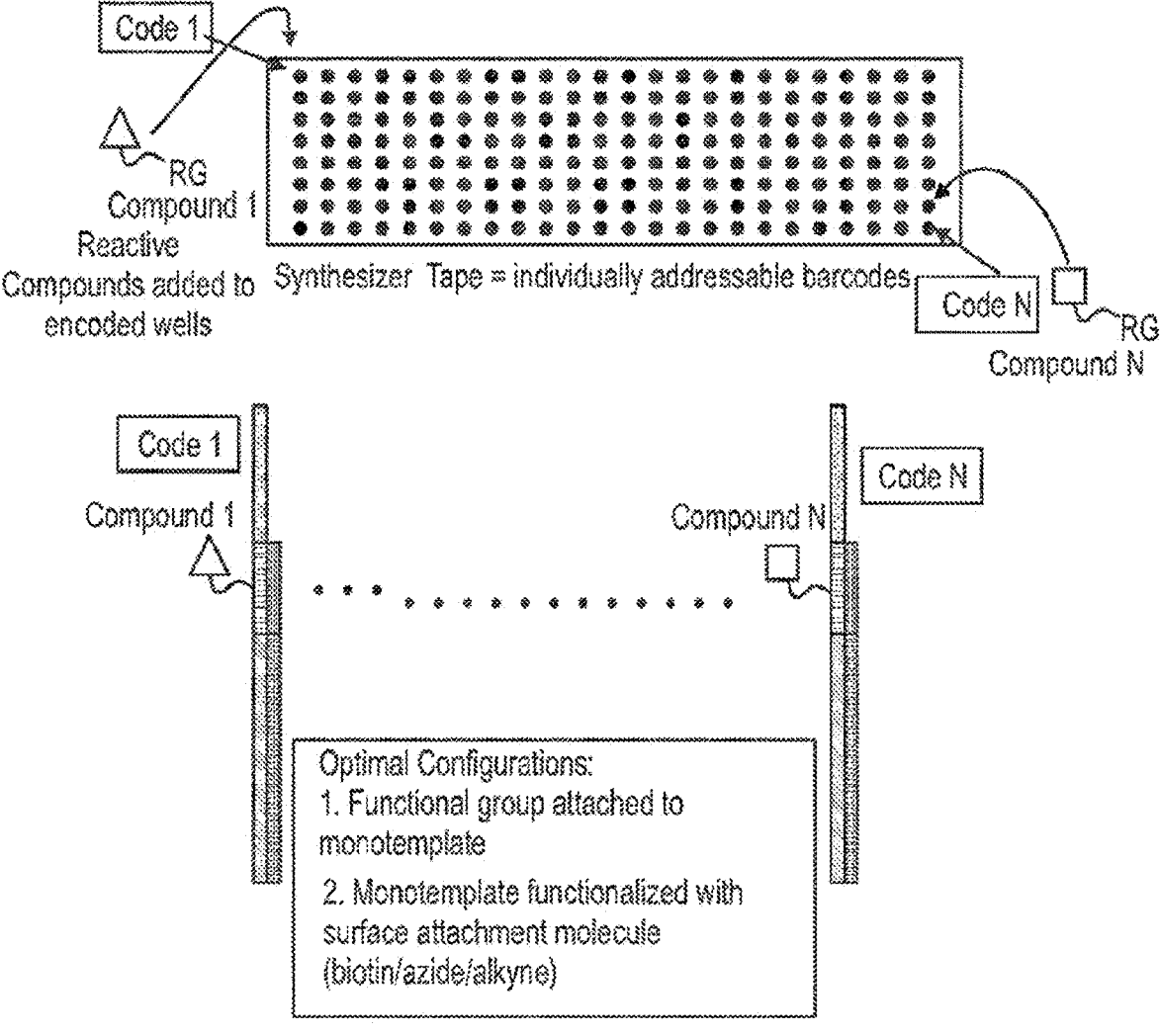

As shown in FIG. 1C, a third step is carried out to robotically add a specific candidate agent (e.g. "compound") to each of the individual wells on the synthesizer tape. Each of the candidate agents includes a reactive group that reacts with the functional group on the different nucleic acids. As a result, each of the candidate agents becomes attached to a particular nucleic acid tag on the synthesizer tape, thereby creating encoded candidate agents.

Figure 1D:
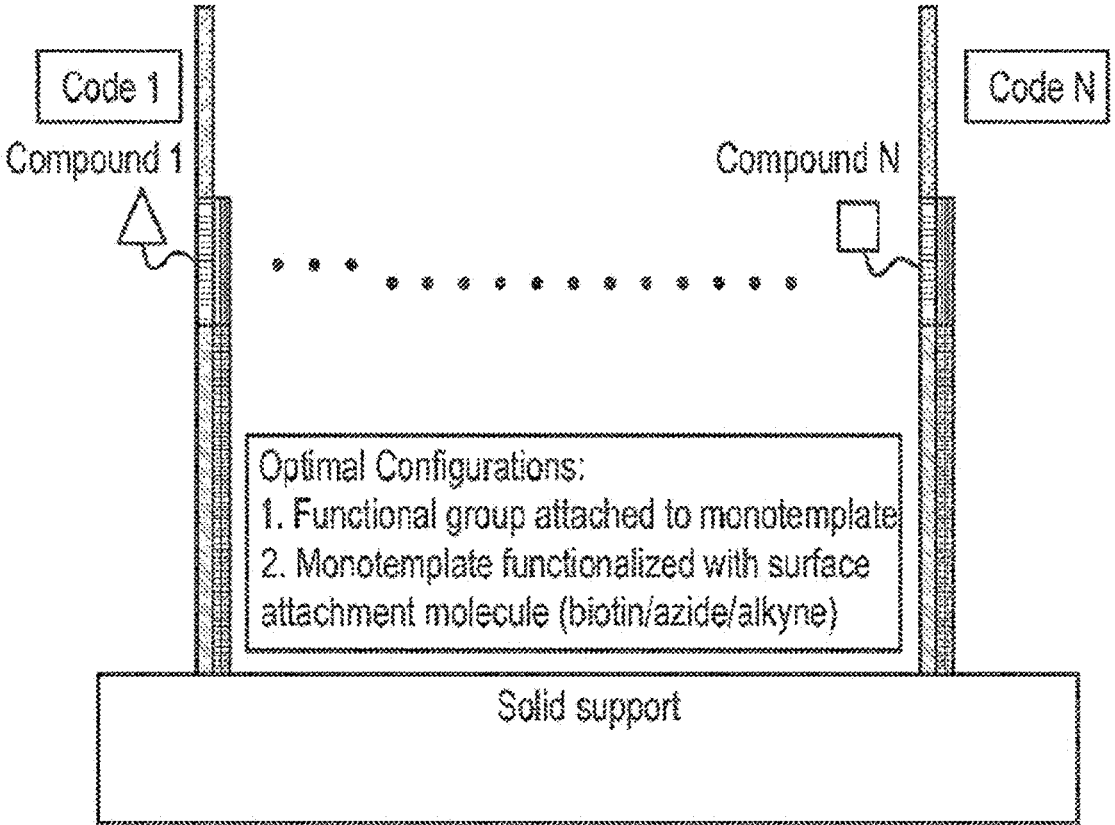

Step 4, as shown in FIG. 1D, is carried out to immobilize the encoded candidate agents at distinguishable sites on a flow cell surface. Immobilization can occur via hybridization of the monotemplate portions of the nucleic acids to complementary universal primers that are on the flow cell surface. The primers can be attached to the flow cell surface via PAZAM gel or other hydrogel as described, for example, in US Pat. App. Pub. No. 2011/0059865 A1, or U.S. Pat. No. 9,012,022, each of which is incorporated herein by reference.

Figure 1E:
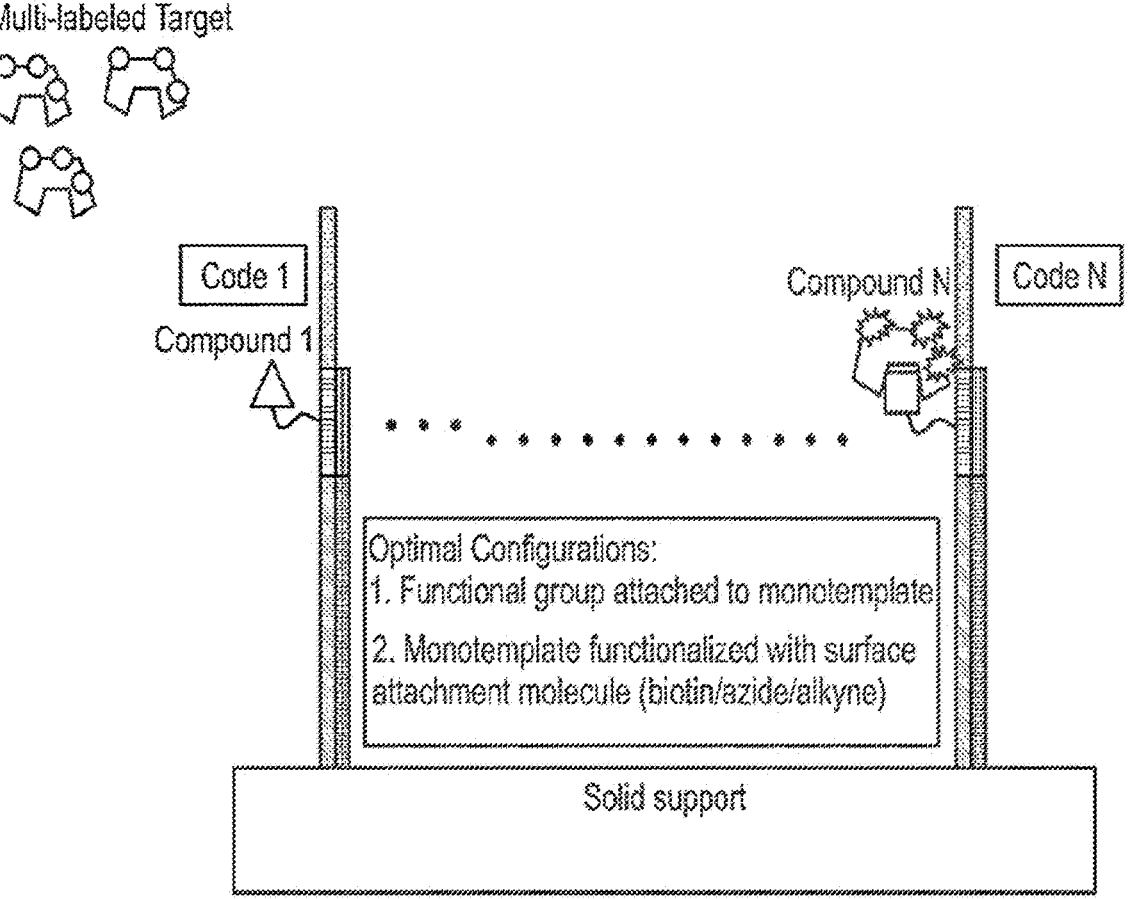

In step 5, as shown in FIG. 1E, a screening agent (also called a "target molecule") is contacted with the immobilized encoded candidate agents that are on the surface of the flow cell. The screening agent includes a fluorescent label that can be detected using an optical device such as an Illumina sequencing instrument. Images can be obtained, for example, in real time to determine binding kinetics for the screening agent at each of the distinguishable sites. In the example of FIG. 1E, the candidate agent attached to code N is a "hit" as determined by a desired binding kinetics profile.

Figure 1F:
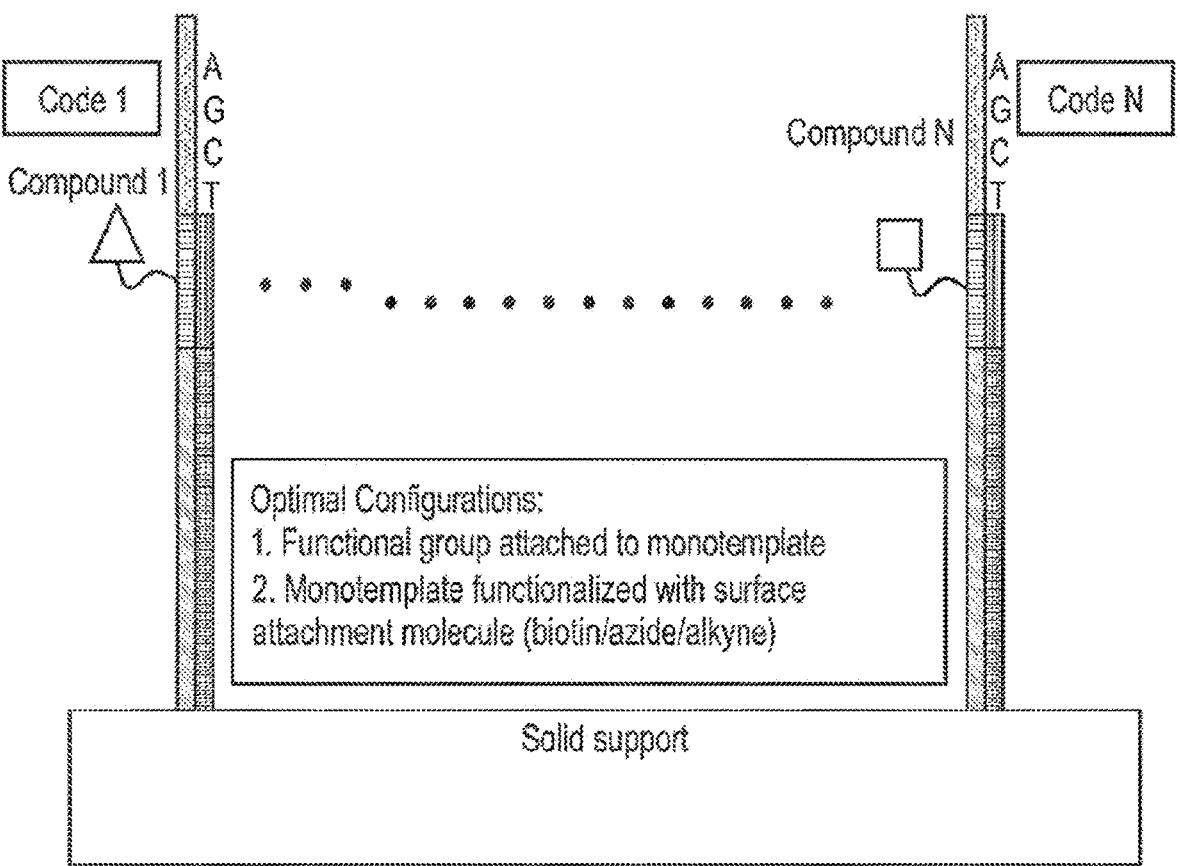

As shown in FIG. 1F, the sequence for code N can be determined based on a sequencing protocol carried out on the flow cell. The sequence for code N can be correlated with the location on the synthesizer tape where it was synthesized and, in turn, the identity of the "hit" can be determined based on knowledge of which candidate agent was delivered to the location on the synthesizer tape where code N was synthesized.

EXAMPLE II

Protein Screening

Solid phase amplification methods allow highly multiplexed presentation of nucleic acids. A particularly useful solid phase amplification method is bridge amplification (also called cluster formation) which can be carried out as described, for example, in U.S. Pat. No. 5,641,658; U.S. Pat. App. Publ. No. 2002/0055100; U.S. Pat. No. 7,115,400; U.S. Pat. App. Publ. No. 2004/0096853; U.S. Pat. App. Publ. No. 2004/0002090; U.S. Pat. App. Publ. No. 2007/0128624; and U.S. Pat. App. Publ. No. 2008/0009420, each of which is incorporated herein by reference.

This example describes using the nucleic acid clusters that result from solid phase amplification to form a protein array on a flow cell. Some key advantages to this technique are (a) it provides a high number of protein-containing features that are relatively small sized yet optically distinguishable on a surface such that a large variety of different proteins can be screened for activity; and (b) the features contain the nucleic acids that encode the protein, the nucleic acids being amenable to sequencing whereby the protein at each feature of the flow cell can be identified.

Figure 2:
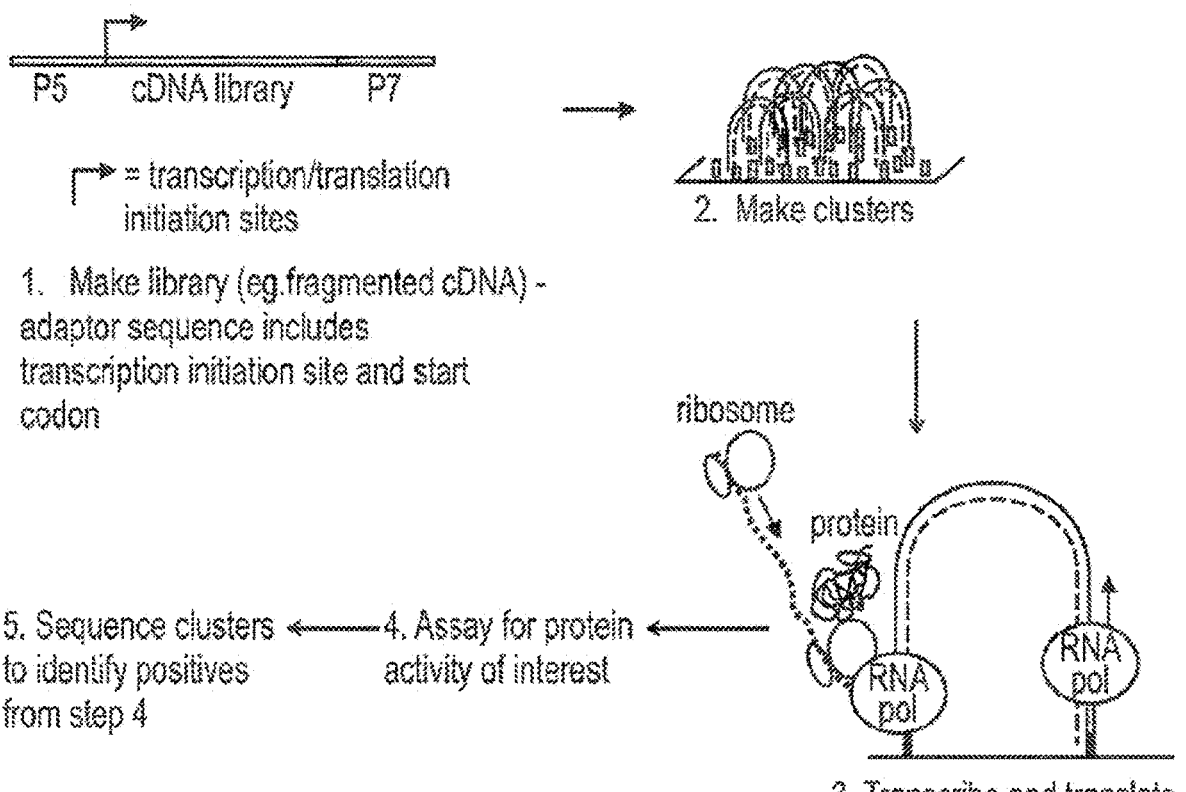
FIG. 2 shows a process for high throughput synthesis and screening of candidate protein agents.

As diagrammed in FIG. 2, a cDNA library is constructed to have adapters with P5 and P7 primer binding sites along with transcription and translation sites. The library is attached to a flow cell and the library members are amplified on the surface of the flow cell using bridge amplification to form clusters. For description P5 and P7 primer binding sequences, methods for making nucleic acid libraries with adapters, and methods for making clusters see, for example, the references cited above in regard to bridge amplification techniques, Bentley et al., *Nature* 456:53-59 (2008), US Pat.

App. Pub. No. 2011/0059865 A1 and U.S. Pat. No. 7,741, 463, each of which is incorporated herein by reference.

The resulting cDNA clusters are transcribed into mRNA using RNA polymerase. The mRNA is maintained in proximity to the cDNA cluster from which it is transcribed by (a) having no transcription termination site at the end of the cDNA construct such that the RNA polymerase stalls and the mRNA transcript remains bound to the cDNA, (b) use of known transcription pause sites (e.g. from Trp operon of E. coli) that will similarly stall the RNA polymerase, (c) employing chemical methods to pause transcription (e.g. bicyclomycin), or (d) having a complementary sequence in the cDNA cluster to which the transcribed RNA will hybridize.

The mRNA, which is localized to the cDNA cluster from which it was transcribed, is then translated to make protein. This will be facilitated by a start codon in the mRNA (which can be introduced along with the transcription initiation sequence in the adapter at the 5' end of the cDNA library construct). Furthermore, the mRNA will not have a stop codon at the 3' end. As diagrammed in FIG. 2, lack of a stop codon leads to ribosome stalling at the end of mRNA, such that the protein remains attached to the mRNA via the ribosome (the mRNA in turn being attached to the cDNA cluster by a stalled RNA polymerase). Alternatively, the ribosomes can be stalled by chemical means (e.g. chloramphenicol/puromycin). Coupled transcription and translation can be performed using readily available rabbit reticulocyte lysate, bacterial S30 or wheat germ extract systems.

In an alternative approach proteins can be generated in solution and then attached to a flow cell or other surface. Although this approach does not include amplification on the surface it can be beneficial when solution based techniques are more readily available or applicable to the protein being evaluated. The resulting array of proteins is screened with a screening agent or other stimulus to identify hits. The cDNA in the clusters is sequenced to identify the protein hits.

EXAMPLE III

Protein Screening Using Tags

Figure 3A:
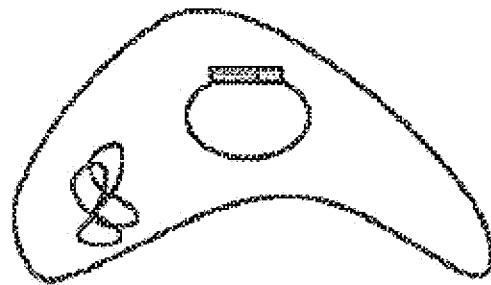
FIG. 3A and FIG. 3B show a process for high throughput tagging, synthesis and screening of candidate protein agents.
Figure 3A:
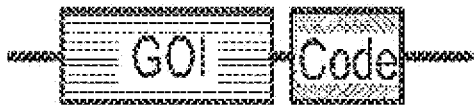

Next Generation sequencing platforms such as those commercialized by Illumina (San Diego, CA) provide a foundation to build an integrated high throughput screening platform for protein evolution. An exemplary method is diagrammed in FIG. 3A and FIG. 3B.

As a first step, a library of vectors is created having random or semi-random mutations to a target protein of interest and random tags (also called "codes"). The vectors are constructed to express an mRNA that includes the coding sequence of the protein and the tag. The number of different random tags exceeds the number of protein variants in the library such that each variant mRNA will have a high probability of including a unique tag. For example, a randomized sequence of 10 nucleotides will provide $10^6$ different tags and a randomized sequence of 20 nucleotides will provide $10^{12}$ different tags.

Alternatively to the random introduction of mutations and the use of random tags, the first step can be performed in a way that predefined mutations are made and associated with known tags.

In a second step, a library of bacteria that have been transformed with the vectors is cultured to produce mRNA from the respective vectors. The library is lysed to release a mixture of mRNA transcripts from the various vectors in the library (i.e. an mRNA library).

In a third step, the mRNA library is split to create two sub-libraries. The library includes multiple copies of each member such that splitting the library results in the same members being present in both sub-libraries. Again, a unique tag sequence is attached to each protein variant sequence.

Figure 3B:
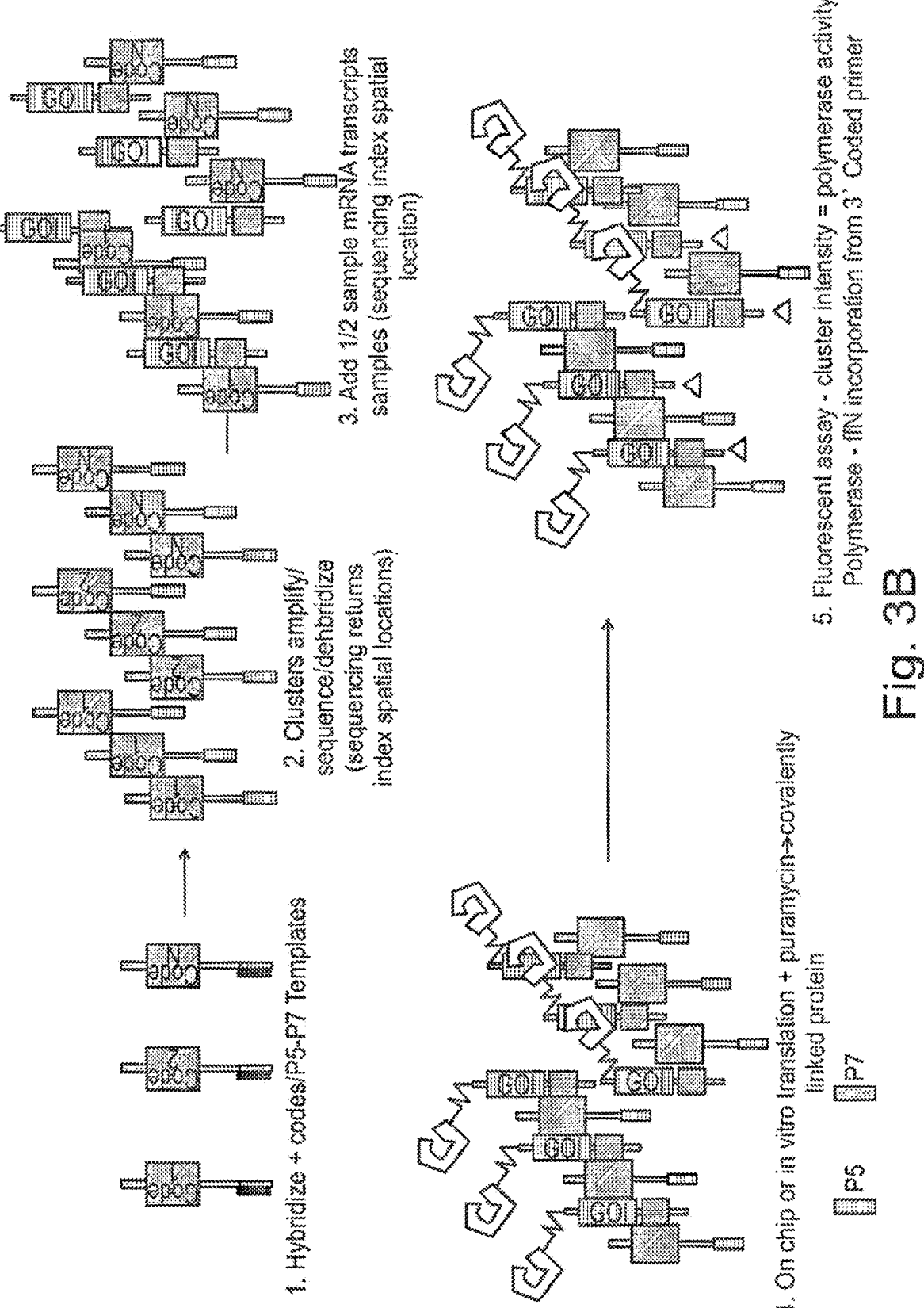

In a fourth step, as shown in FIG. 3B, the first sub-library is attached to a flow cell, amplified on the flow cell, and the coding sequences and respective tags of the resulting amplicons are sequenced. In this way the site where each member is attached is located. Then the members of the second sub-library are contacted with the flow cell to allow members from the second sub-library to hybridize to amplicons generated from the identical members from the first sub-library via the complementarity of the tag sequences. In this way the site where each member of the second sub-library is located can be inferred based on the sequencing results and the expected hybridization between tags and their complements. The members of the second sub-library, having been captured on the flow cell, are then translated to express the protein targets on the flow cell. Each of the proteins is expressed in a way that it remains attached to the RNA from which it was translated. For example, attachment can be achieved using techniques set forth in Example II. The proteins are then screened with a screening agent or other stimulus allowing a desired function to be identified in a high throughput fashion. The result is a protein activity signal that is localized to a site on the flow cell that is correlated with the RNA sequence encoding the protein.

This methodology can allow for high throughput of 30 million proteins per flow cell lane or more. This screening process avoids challenges associated with emulsion based screening. For example, quantitative and kinetic-based data can be obtained at each feature on the flow cell using an Illumina sequencing instrument to allow a more refined and selective screening criteria than available using traditional emulsion based techniques.

EXAMPLE IV

Cell Screening

This example describes a methodology for screening cells that provides the high throughput advantages of fluorescence activated cell sorting (FACS) with the ability to follow dynamic processes in real time, an advantage typically associated with fluorescence microscopy, while adding the advantages of next-generation sequencing to identify individual cells in the population. As a result the methods set forth herein allow recovery and characterization of cells that display a desired behavior. Specifically, this example adapts a next generation sequencing platform from Illumina Inc. (San Diego, CA) to monitor by fluorescence, the phenotypic behavior (e.g. measured by expression of fluorescent reporters) of individual cells in response to specific stimuli at ultra-high throughput, followed by sequencing of tags displayed on the surface of each individual cell for subsequent identification and recovery. This platform can provide a standard method for high-throughput screening for cellular engineering.

Cells have potential therapeutic capabilities that are different from, and in many cases an improvement over, those of small molecules and proteins. Cells can actively move to specific locations in the body, they can sense multiple external stimuli, and they can integrate multiple sources of information to respond with precise outputs. In addition, cell-based responses can have complex dynamic patterns that can be controlled by pre-programmed functions or by the addition of external factors. Currently, cell-based therapies are being explored for the treatment of a wide range of disease, from the use of engineered microorganisms to treat Crohn's disease to the use of patient-derived engineered human immune cells to treat cancer. Importantly, either microorganisms or human cells can be engineered to be therapeutically useful.

Workflow for Cell Engineering

Cellular engineering (either in microbial or human cells) is a complex process with many variables to consider. Thus, rather than attempting single designs, it is beneficial to design libraries of candidate cells that can then be selected or screened. Specifically, cell engineering can include the following steps: (1) design of genetic circuits that can include one or more sensors for external signals, an information integrating network, and a signal-dependent response (the response often involving gene expression); (2) modifying one or more genetic targets for the above mentioned components across a library of candidate cells (e.g. using CRISPR-Cas9); and (3) high throughput screening to identify hits, among the numerous different candidate cells, that confer desirable cellular behaviors.

A robust and high throughput screening technique can provide significant advantages to cell engineering, as the number of cells that need to be tested is large (often thousands of different designs are tried) and a large and varied panoply of cellular behaviors will manifest due to modifications introduced in the engineering process. A desirable screen will also be capable of following complex temporal dynamics while achieving very high throughput. The screen set forth herein provides these advantages.

Figures 4, 5:
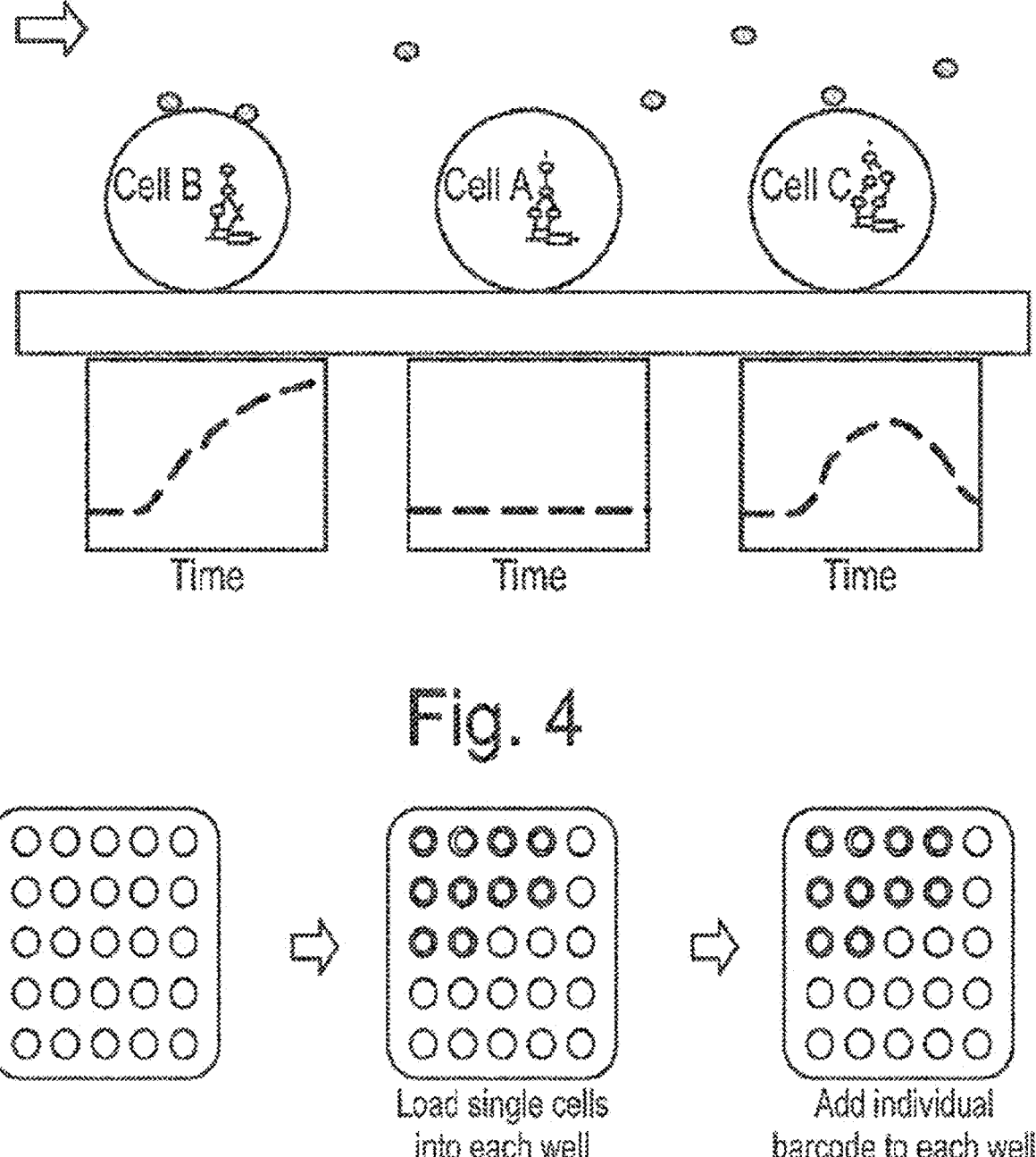
FIG. 4 shows exposure of a screening agent to cells that are attached to a flow cell and plots of fluorescence vs. time expected from various cell responses to the screening agent.
FIG. 5 shows cells sorted into individual microwells and then tagged with microwell-specific tags.

The cell screening method has the following two stages:

Stage 1: Phenotypic Monitoring. A library of live engineered cells with suitable fluorescence reporters is loaded into a flow cell for a sequencing platform (e.g. Illumina MiSeq®, NextSeq®, HiSeq® or Genome Analyzer® platform), as shown in FIG. 4. Individual cells will be randomly distributed and attached to the surface of the flow cell (using specific attachment chemistries depending on the particular cells to be analyzed). Fluorescence of each individual cell is recorded at defined time intervals, scanning the flow cell surface as currently done for Illumina flow cells during sequencing. Note that individual cells will have average sizes comparable to (or larger than) current sequencing clusters, thereby making the resolution of the sequencing platform well suited to the screen. Also, cells can carry thousands of fluorescent reporter molecules, such that signal intensities will be similar (or larger) than those currently detected by sequencing platforms. At specific times, the cells are exposed to screening agents (or other stimuli) and the response of the cells (e.g. as reflected in changes in expression of reporter genes, or changes in fluorescence intensity of any other type of cell reporter-such as Calcium concentration in cytoplasm, fluorophore quenching by changes in subcellular localization, etc.) is detected. By monitoring changes in fluorescent reporters over time, it will be possible to determine the temporal dynamics of the phenotypic changes in response to diverse stimuli (or combinations of stimuli).

Stage 2: Single Cell Identification by Decoding of Individual tags. Each cell in the population will be assigned a tag. Three different techniques for tagging cells are described below. In a first step tags are attached to individual cells. Independently of the type of tag (e.g. bead, membrane-attached nucleic acid, etc.), cells are first sorted to individual vessels (e.g. microwells) such that one cell is located in each vessel. Then a unique tag is provided to the cell in each Vessel as shown in FIG. 5.

Figure 6:
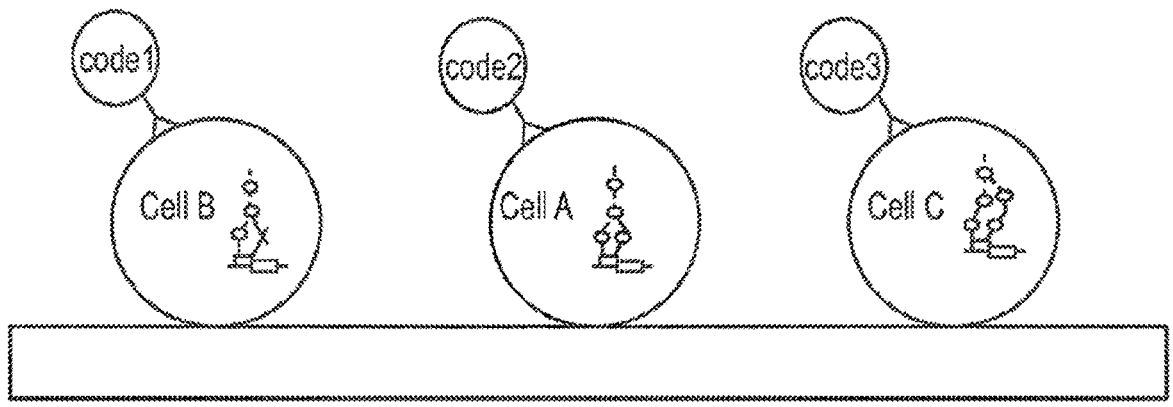
FIG. 6 shows decoding of cell locations on a solid support using coded beads.

2.1 Single Cell Barcoding with Beads. Each cell in the population (e.g. ~ 10 μm diameter for T cells) are tagged with 1 to 10 beads. The beads can have a diameter of about 1-2 μm. Useful beads include for example, those used in Illumina's BeadArray Technology or described in U.S. Pat. Nos. 7,622,294 or 8,741,630, each of which is incorporated herein by reference. Each cell will be tagged with beads encoding a single tag, by previously isolating individual cells into individual vessels, and adding to each vessel beads sharing the same unique tag (i.e. there will be a known correspondence between each vessel and each tag). Cell tagging could be achieved in a number of ways, for example by covalently linking the beads with antibodies that recognize specific epitopes naturally present on the surface of the target cells. Note that in this way, though each bead-tagged cell will be randomly distributed on the surface of the flow cell, each cell will be spatially co-localized with its own bead(s) (FIG. 6). Thus, following Stage 1, the identity of each cell will be revealed by decoding the bead(s) on the flow cell and assigning identified tags to the cell in closest proximity to the corresponding bead(s). The tags on the beads can be decoded using a sequencing by synthesis technique (see, for example, Bentley et al., *Nature* 456:53-59 (2008), PCT Publ. Nos. WO 91/06678, WO 04/018497 or WO 07/123744; U.S. Pat. Nos. 7,057,026, 7,329,492, 7,211,414, 7,315,019 or 7,405,281, and US Pat. App. Publ. No. 2008/0108082 A1, each of which is incorporated herein by reference) or a decoding technique set forth in U.S. Pat. No. 8,460,865 or Gunderson et al., *Genome Research* 14:870-877 (2004), each of which is incorporated herein by reference.

2.2 Single Cell Identification with Sequence Tags. An alternative or addition to bead tagging is to use unique sequence identifiers directly displayed on the surface of each cell. For that, each cell in the population will be modified with surface-displayed individual single-stranded DNA tags prior to cell loading into the flow cell (e.g. prior to Stage 1). Nucleic acid tag attachment chemistry will depend on the particular cell type. For example, human cells can be tagged with single stranded DNA molecules covalently linked to plasma membrane lipids, as reported by Sleden et al., *J Am Chem Soc* 134:765-8 (2012), which is incorporated herein by reference. As another example, yeast cells can be tagged with single stranded DNA molecules covalently linked to HaloTag proteins displayed on Aga1-Aga2 cell wall complexes.

Each individual tag is composed of at least three regions. Region 1 is connected to an attachment moiety (e.g. lipid or protein, depending on the cell type). Region 2 consists of a defined number of bases that depends on the plexity required (using all 4 nucleotides it is possible to generate $4^n$ combinations for a sequence of length "n"; e.g. a 4 base-long sequence will encompass tags for the identification of 256 different individual cells, 5 will result in 1024 different tags, etc.). Thus, with as little as 9-base tag sequence it will be possible to individually identify more than 250,000 different cells. Region 3 consists of a DNA sequence complementary to a sequencing primer. Note that each cell will be tagged with nucleic acids encoding a single tag, by previously isolating individual cells in vessels, and adding to each vessel nucleic acids sharing the same unique tag sequence (as before, there will be a known correspondence between each vessel and each tag).

In a separate step (carried out before or after phenotypic measurements have been obtained), the identity of each individual cell will be determined, for example, in one of two ways, described below.

Figure 7:
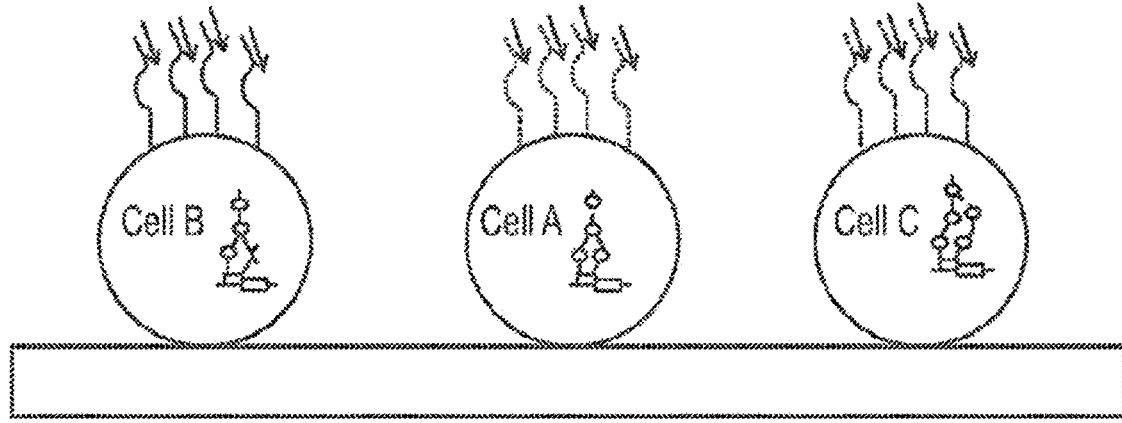
FIG. 7 shows decoding of cell locations on a solid support using nucleic acid tags.

2.2.1 In situ Sequencing of the Particular Tag Attached to Each Cell. Each cell will display multiple copies of a particular tag. Thus, the signal is readily detectable on a sequencing instrument (See FIG. 7). Furthermore, the read length to identify each tag is relatively short (e.g. 9 bases suffice to identify >250,000 tags) well within the read lengths of hundreds of nucleotides typical from commercially available sequencing instruments.

In situ tag sequencing can be achieved in a number of ways. One possibility is to sequence directly on the surface of live cells. Another possibility is to fix the cells prior to sequencing (in case nucleotides leaking from live cells interfere with the sequencing reaction). A third possibility is to detach and capture the nucleic acid tags from each cell. For this, the flow cell surface is modified with capture probe (e.g. a sequencing primer) containing a region complementary to a region common to all cell-attached nucleic acids, allowing initial attachment of the cells to the surface, and facilitating the capture of the detached nucleic acids prior to sequencing. Optionally, the cells can be removed following surface capture of the nucleic acid tags.

Figure 8:
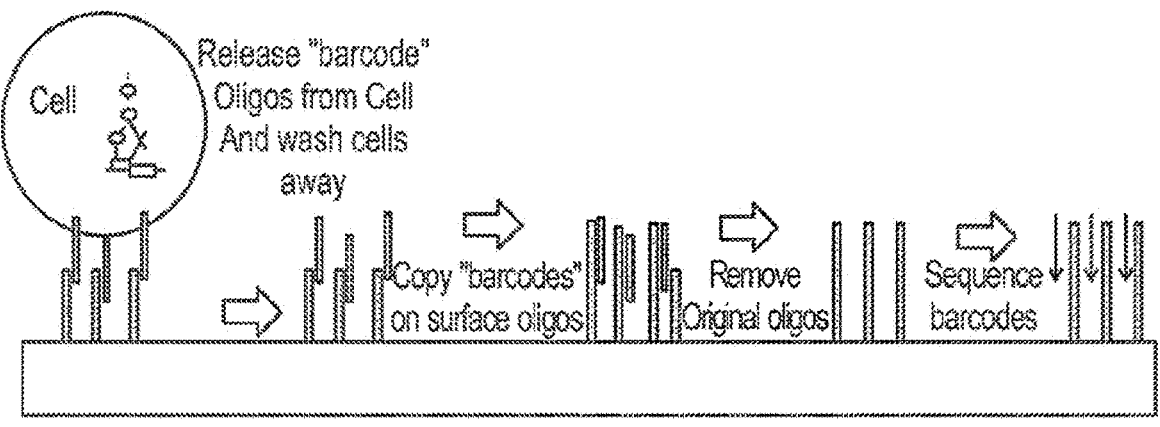
FIG. 8 shows transfer of nucleic acids tags from a cell to a site on a solid support and sequencing of the nucleic acid tag on the solid support.

2.2.2. In situ Sequencing of Copies of Tags Attached to the Flow Cell. As shown in FIG. 8, cell-surface displayed nucleic acid tags are hybridized to flow cell-surface attached primers (with partial complementary sequences). Cell-surface nucleic acid tags are detached from the cells by digestion with specific restriction enzyme, and cells are then washed out of the flow cell. Flow cell-surface attached nucleic acid tags will then be extended, effectively creating copies of the original cell tags, which will then be sequenced. In many cases there won't be a need to bridge-amplify the copies, as a cell is likely to leave a "spot" of about 1 µm diameter composed of thousands of nucleic acids. However, bridge amplification can be carried out if desired (in which case appropriate primer binding sites can be added to the nucleic acid tags and a second primer type can be attached to the flow cell surface).

In some cases, a tag can be attached to an individual cell using a membrane-anchored nucleic acid, as shown in FIG. 9. The membrane anchored nucleic acid will include a linker region, a restriction site (RE), sequencing primer binding site (SBS3), tag sequence (barcode) and capture sequence. Cells can then be surface-captured by surface-attached nucleic acids with a sequence complementary to the capture sequence, as described in Sleden et al., *J Am Chem Soc* 134:765-8 (2012), which is incorporated herein by reference, or as shown in FIG. 10.

Following the recording of fluorescence signals indicative of cell phenotypic behavior in a screening step (e.g. measuring fluorescence from a reporter over a period of time and under specific media conditions), the nucleic acid tags can be copied on the flow cell surface and then the cells can be washed away. The copies on the surface effectively preserve spatial information regarding which cells were located where on the flow cell surface, as shown in FIG. 11.

By recording the spatial location of each cell on the surface it will be possible to assign tag identities to each of the recorded fluorescence time-series, thus effectively connecting phenotypic responses with cell identity. These identities can then be used to either identify individual clones in single vessels (where cells were initially tagged, as shown in FIG. 12), or to recover selected cells from cell mixtures by pull down with nucleic acids that are complementary to the tags present on the surface of the selected cells.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method of characterizing a plurality of cells, comprising:
   (a) contacting a substrate with a plurality of cells to form an array of cells, wherein the substrate is a component of a flow cell;
   (b) contacting the array of cells with one or more reporter molecules;
   (c) detecting the one or more reporter molecules using a nucleic acid sequencing device comprising imaging optics;
   (d) identifying a phenotypic cellular characteristic of a cell within the array of cells based on the detecting of the one or more reporter molecules, wherein the phenotypic cellular characteristic is an optically detectable characteristic;
   (e) synthesizing at least one nucleic acid complementary to one or more nucleic acid tags associated with the cell within the array of cells, wherein the synthesizing comprises a plurality of cycles in which one or more types of nucleotides contact the one or more nucleic acid tags;
   (f) detecting, over the plurality of cycles, the one or more types of nucleotides contacting the one or more nucleic acid tags using the imaging optics of the nucleic acid sequencing device;
   (g) determining a nucleic acid sequence of the one or more nucleic acid tags based on the detecting of the one or more types of nucleotides; and
   (h) characterizing the cell within the array of cells based on the phenotypic cellular characteristic and the nucleic acid sequence of the one or more nucleic acid tags, wherein the characterizing comprises determining a cellular behavior.

2. The method of claim 1, wherein the plurality of cells are selected from the group consisting of natural cells isolated from a multicellular organism, natural cells that comprise single cell organisms, genetically engineered cells, and cultured cells.

3. The method of claim 2, wherein the plurality of cells are stem cells or immune cells.

4. The method of claim 1, wherein the plurality of cells are live cells.

5. The method of claim 4, further comprising culturing the plurality of cells on the substrate.

6. The method of claim 1, wherein detecting the one or more reporter molecules comprises detecting a luminescent signal.

7. The method of claim 6, wherein the one or more reporter molecules interact with the cell within the array of cells by attachment to a plasma membrane lipid, a fatty acid, or a protein on a cell surface.

8. The method of claim 1, wherein step (a) further comprises spatially resolving the array of cells on the substrate.

9. The method of claim 1, wherein the array of cells are arranged on the substrate in a grid.

10. The method of claim 1, wherein the array of cells are arranged on the substrate in an irregular pattern.

11. The method of claim 10, wherein the array of cells are arranged on the substrate in a non-repeating pattern.

12. The method of claim 1, wherein the one or more nucleic acid tags comprises an antibody or a nucleic acid having specific binding affinity for a cellular component.

13. The method of claim 12, wherein the one or more nucleic acid tags is attached to the cell of the array of cells by interacting with a protein or component in a plasma membrane lipid of the cell.

14. The method of claim 1, wherein the one or more nucleic acid tags comprises a universal primer binding sequence capable of being sequenced.

15. The method of claim 1, wherein the method comprises:
(i) acquiring optical signals emitted from the one or more reporter molecules at several time points;
(ii) acquiring sequencing information of the one or more nucleic acid tags at several time points; or
(iii) both (i) and (ii),
wherein a change in the optical signals or the sequencing information is detected over time.

16. The method of claim 1, further comprising amplifying the one or more nucleic acid tags to produce amplicons of the one or more nucleic acid tags.

17. The method of claim 16, wherein synthesizing the at least one nucleic acid complementary to the one or more nucleic acid tags comprises synthesizing nucleic acids complementary to the amplicons of the one or more nucleic acid tags.

18. The method of claim 17, further comprising attaching the amplicons of the one or more nucleic acid tags to the substrate prior to sequencing.

19. The method of claim 18, wherein the amplicons of the one or more nucleic acid tags can be spatially resolved during sequencing on the substrate.

20. The method of claim 1, wherein the detecting of the one or more types of nucleotides comprises detecting optical signals indicative of the one or more types of nucleotides.

21. The method of claim 1, wherein the method further comprises contacting the array of cells with a stimulus.

22. The method of claim 21, wherein the array of cells are characterized before and after contacting the cells with the stimulus.

23. The method of claim 22, wherein the method comprises:
(i) acquiring optical signals emitted from the one or more reporter molecules at one or more time points before and one or more time points after contacting the array of cells with the stimulus; and
(ii) comparing the optical signal acquired at the one or more time points before contacting the array of cells with the stimulus to the optical signal acquired at the one or more time points after the array of cells is contacted with the stimulus.

24. The method of claim 1, wherein the detecting of step (f) is by sequencing by synthesis.

* * * * *